US008906002B2

(12) United States Patent
Kishi et al.

(10) Patent No.: US 8,906,002 B2
(45) Date of Patent: Dec. 9, 2014

(54) BENDING JOINT MECHANISM, SURGICAL INSTRUMENT HAVING THIS BENDING JOINT MECHANISM, AND MANIPULATOR HAVING THIS BENDING JOINT MECHANISM

(71) Applicant: Olympus Corporation, Tokyo (JP)

(72) Inventors: Kosuke Kishi, Hachioji (JP); Ryoji Hyodo, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/802,026

(22) Filed: Mar. 13, 2013

(65) Prior Publication Data

US 2013/0197492 A1 Aug. 1, 2013

Related U.S. Application Data

(63) Continuation of application No. PCT/JP2011/058107, filed on Mar. 30, 2011.

(30) Foreign Application Priority Data

Sep. 30, 2010 (JP) .................................. 2010-222976
Feb. 15, 2011 (JP) .................................. 2011-030103

(51) Int. Cl.
*A61B 17/00* (2006.01)
*A61B 19/00* (2006.01)
(52) U.S. Cl.
CPC .................. *A61B 17/00* (2013.01); *A61B 19/22* (2013.01)
USPC ............................................. 606/1; 606/130

(58) Field of Classification Search
USPC ...................... 606/1, 130, 138, 139, 151, 160, 606/166–182, 205–211; 604/19–22; 600/562–568
See application file for complete search history.

(56) References Cited

U.S. PATENT DOCUMENTS

| 5,086,541 | A | | 2/1992 | Auternaud et al. |
| 5,379,664 | A | * | 1/1995 | Kershaw et al. ........... 74/490.05 |
| 5,797,900 | A | * | 8/1998 | Madhani et al. .................. 606/1 |
| 5,828,813 | A | * | 10/1998 | Ohm ............................. 700/260 |
| 6,746,443 | B1 | * | 6/2004 | Morley et al. ..................... 606/1 |
| 6,913,613 | B2 | * | 7/2005 | Schwarz et al. .............. 606/206 |
| 7,955,321 | B2 | * | 6/2011 | Kishi et al. ......................... 606/1 |

(Continued)

FOREIGN PATENT DOCUMENTS

| EP | 2 014 252 A2 | 1/2009 |
| JP | 63-10088 | 1/1988 |

(Continued)

OTHER PUBLICATIONS

European Search Report dated Jun. 14, 2013 from corresponding European Patent Application No. 11 82 8511.3.

(Continued)

*Primary Examiner* — Ahmed Farah
(74) *Attorney, Agent, or Firm* — Scully, Scott, Murphy & Presser, P.C.

(57) ABSTRACT

A bending joint mechanism includes a joint section. The joint section includes a shaft section, an actuating section, a coupling member and a rod section. The rod section has an elastic portion which is elastically deformable in directions other than the axial direction of the shaft section.

15 Claims, 17 Drawing Sheets

(56) References Cited

U.S. PATENT DOCUMENTS

| | | | |
|---|---|---|---|
| 2002/0111621 A1* | 8/2002 | Wallace et al. | 606/41 |
| 2004/0199147 A1* | 10/2004 | Nishizawa et al. | 606/1 |
| 2006/0155262 A1 | 7/2006 | Kishi et al. | |
| 2007/0208375 A1 | 9/2007 | Nishizawa et al. | |
| 2008/0310945 A1 | 12/2008 | Tsujita et al. | |
| 2011/0213346 A1* | 9/2011 | Morley et al. | 606/1 |

FOREIGN PATENT DOCUMENTS

| | | |
|---|---|---|
| JP | 8-164144 | 6/1996 |
| JP | 2002-263109 | 9/2002 |
| JP | 2004-122286 | 4/2004 |
| JP | 2006-191939 | 7/2006 |
| JP | 2008-307310 | 12/2008 |
| WO | 2009/145572 A2 | 12/2009 |

OTHER PUBLICATIONS

International Preliminary Report on Patentability together with the Written Opinion dated Apr. 18, 2013 received in related International Application No. PCT/JP2011/058107.

International Search Report dated Jul. 12, 2011 issued in corresponding International Application No. PCT/JP2011/058107.

* cited by examiner

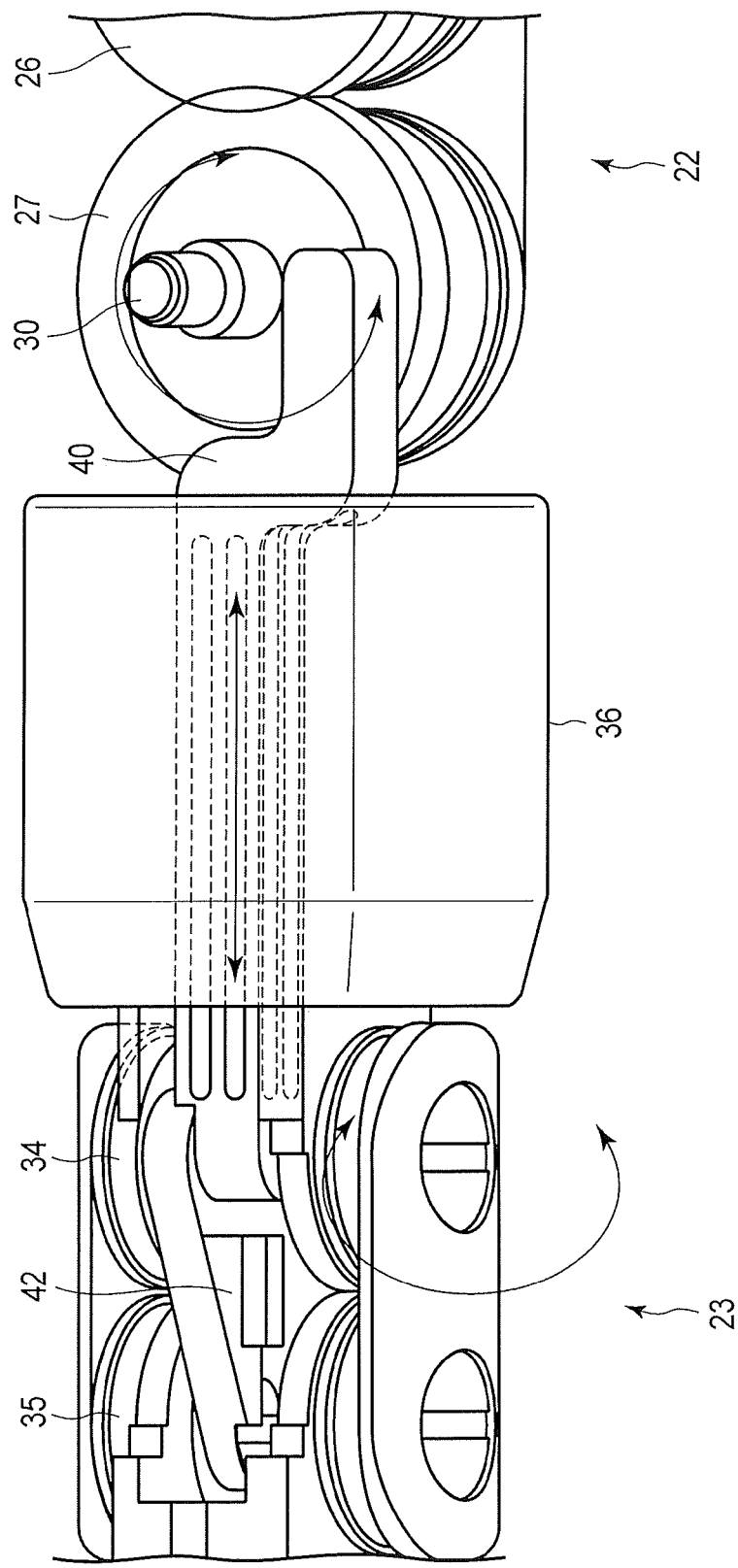
F I G. 8

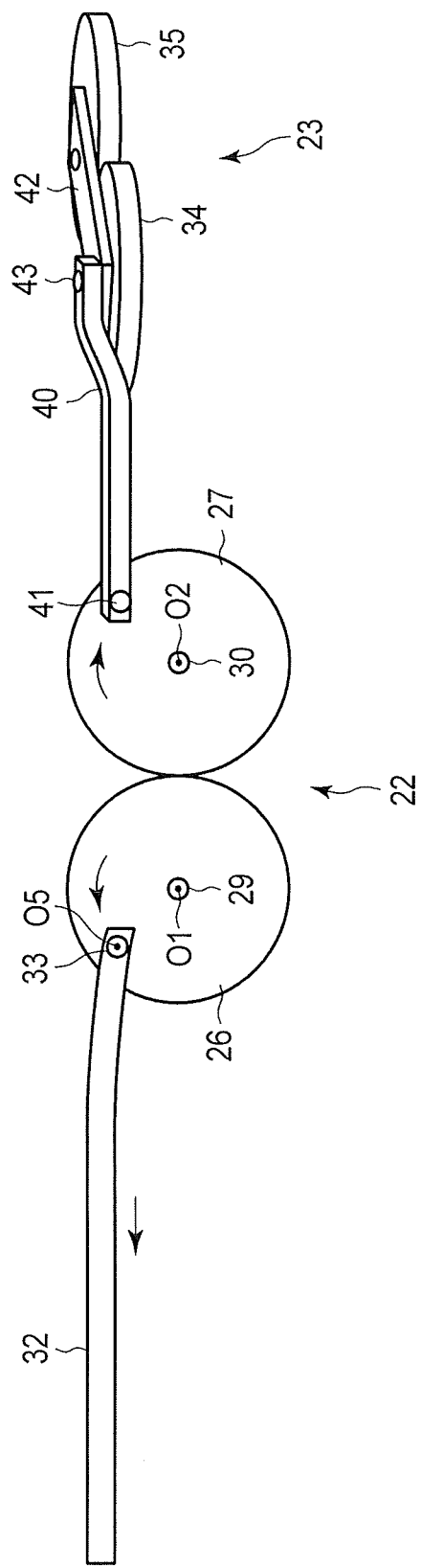
F I G. 9B

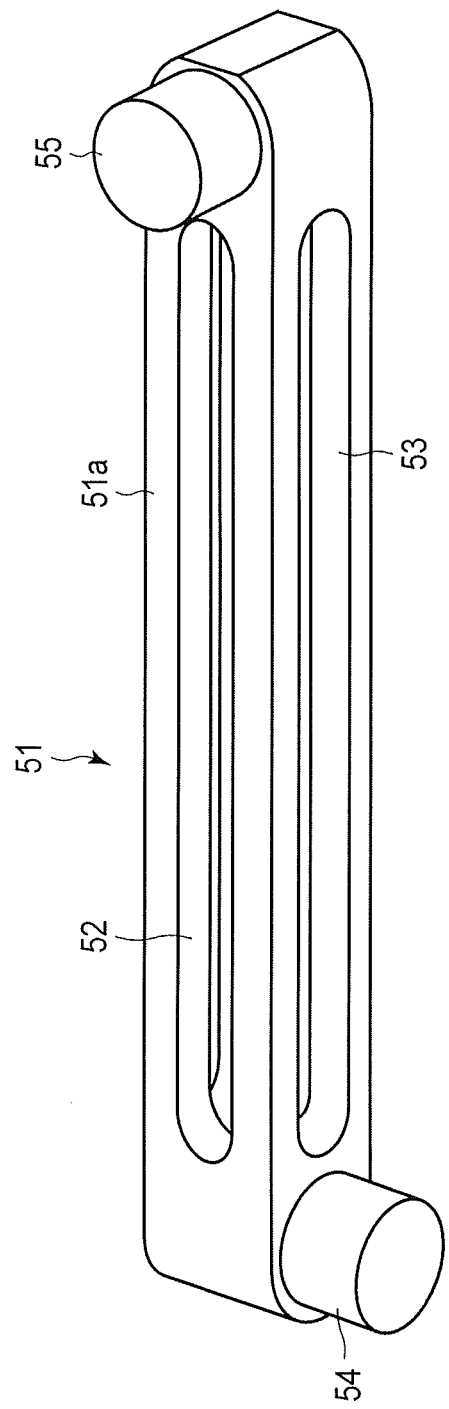
F I G. 10A

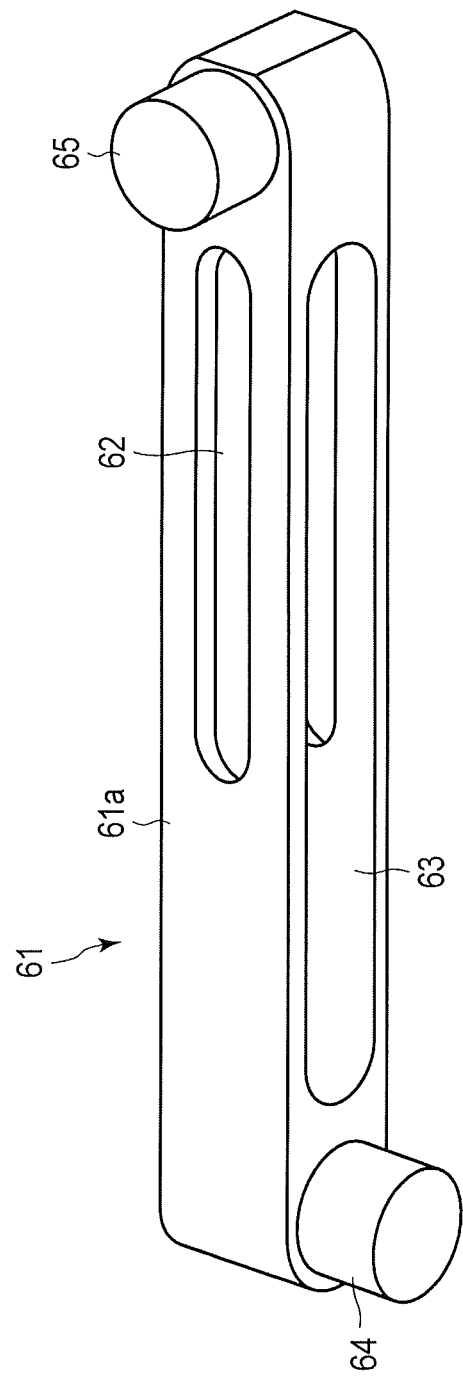
F I G. 10B

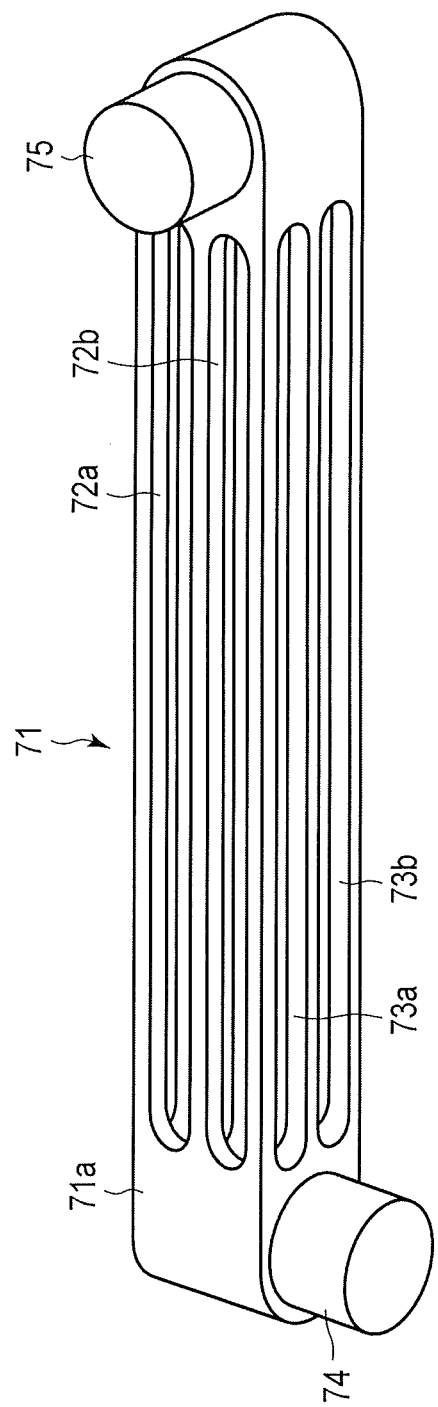
F I G. 10C

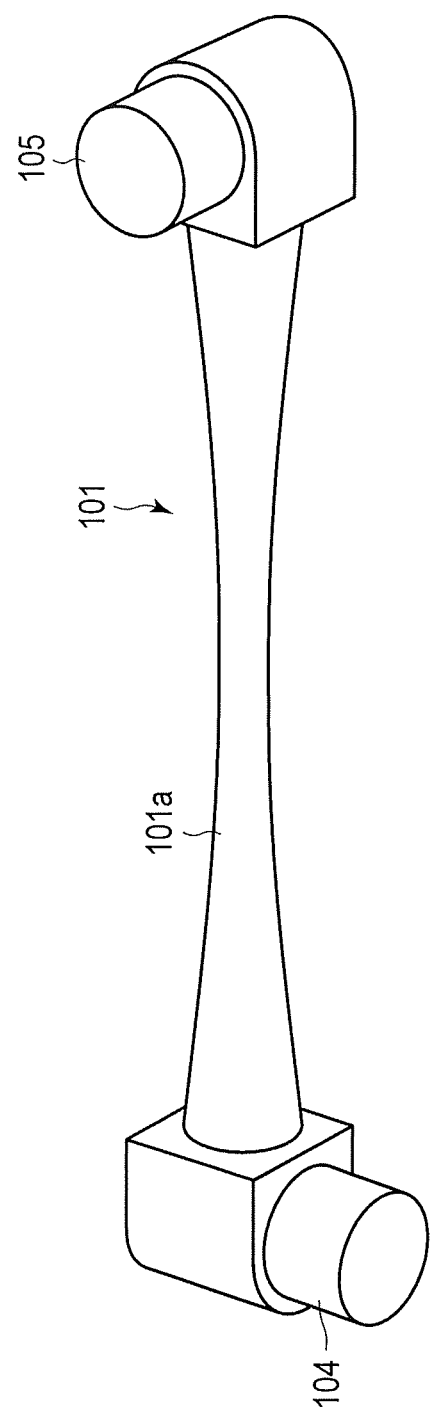
F I G. 10F

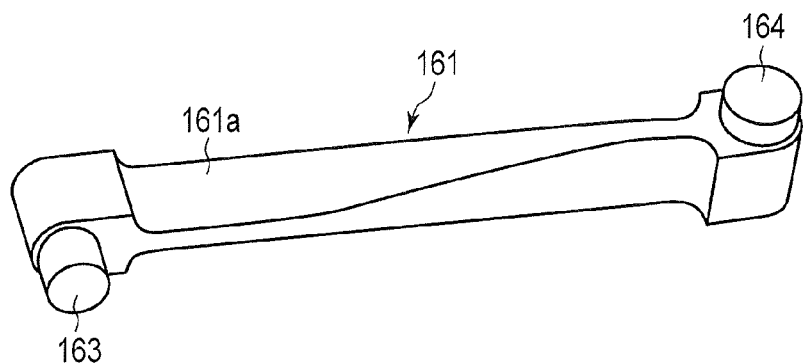
F I G. 10H
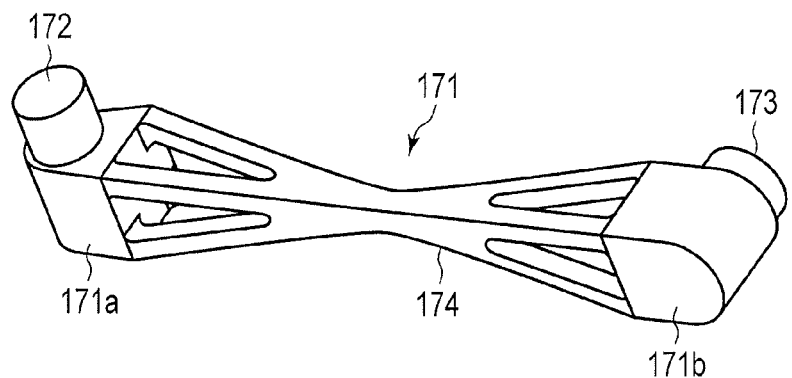
F I G. 10I
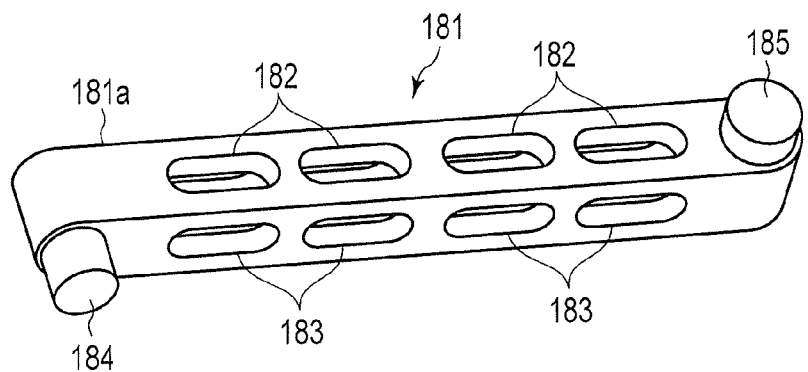
F I G. 10J

BENDING JOINT MECHANISM, SURGICAL INSTRUMENT HAVING THIS BENDING JOINT MECHANISM, AND MANIPULATOR HAVING THIS BENDING JOINT MECHANISM

CROSS-REFERENCE TO RELATED APPLICATIONS

This application is a Continuation application of PCT Application No. PCT/JP2011/058107, filed Mar. 30, 2011 and based upon and claiming the benefit of priority from prior Japanese Patent Applications No. 2010-222976, filed Sep. 30, 2010; and No. 2011-030103, filed Feb. 15, 2011, the entire contents of all of which are incorporated herein by reference.

BACKGROUND OF THE INVENTION

1. Field of the Invention

The present invention relates to a bending joint mechanism used in a multidegree-of-freedom surgical instrument, a surgical instrument having this bending joint mechanism, and a manipulator having this bending joint mechanism.

2. Description of the Related Art

There has heretofore been known a joint drive device that uses wires to drive joint sections of a treatment instrument such as a multidegree-of-freedom surgical instrument. In this mechanism, problems occur in durability, maintenance, and controllability, such as stretching, loosening, or cutoff by fatigue of the wires. Moreover, in this mechanism, it is difficult to transmit power through bending joint portions to farther joints.

To solve this problem, for example, Jpn. Pat. Appln. KOKAI Publication No. 2008-307310 has disclosed a drive mechanism for driving a joint mechanism. The joint mechanism comprises a double rotation guide having two rolling guides. The drive mechanism serves as a translation cam mechanism which is driven, for example, by a parallel link or by a rack and pinion. Means shown in Jpn. Pat. Appln. KOKAI Publication No. 2008-307310 is provided with the two rolling contact guides, and a plate for bending which keeps the rotation centers of the guides at a distance and which rolls one guide, whereby a bending joint is obtained.

Furthermore, in this translation cam mechanism, a wire is put on a pulley around the rotation center of the guide. In this way, power is transmitted to a driven portion following the bending joint by the wire without interference with the operation of the bending joint.

BRIEF SUMMARY OF THE INVENTION

According to an aspect of embodiments, a bending joint mechanism includes a joint section, the joint section includes a shaft section which has an arc-shaped first rotation guide portion around a first rotation center and which has an axis that intersects at right angles with the axis of the first rotation center, an actuating section having an arc-shaped second rotation guide portion around a second rotation center, the second rotation guide portion coming in rolling contact with the first rotation guide portion at a proximal end portion thereof, a coupling member which is rotatably coupled at a distal end portion thereof to the second rotation center and which is rotatably coupled at a proximal end portion thereof to the first rotation center and a rod section which is provided translatability relative to the shaft section in the axial direction of the shaft section and which is coupled at a distal end portion thereof to a position other than the first rotation center of the coupling member and which translate in the axial direction of the shaft section in response to a driving force, wherein the bending joint mechanism turns the second rotation guide portion around the first rotation center along the first rotation guide portion via the coupling member together with the translating of the rod section to bend the actuating section relative to the shaft section, and the rod section has an elastic portion which is elastically deformable in directions other than the axial direction of the shaft section.

According to an aspect of embodiments, a bending joint mechanism includes a first joint section, the first joint section includes a first shaft section which has an arc-shaped first rotation guide portion around a first rotation center and which has an axis that intersects at right angles with the axis of the first rotation center, a first actuating section having an arc-shaped second rotation guide portion around a second rotation center, the second rotation guide portion coming in rolling contact with the first rotation guide portion at a proximal end portion thereof, a first coupling member which is rotatably coupled at a distal end portion thereof to the second rotation center and which is rotatably coupled at a proximal end portion thereof to the first rotation center, a first rotation gear which has the same axis and radius of a rotation center as the axis and radius of the first rotation center of the first rotation guide portion and a second rotation gear which has the same axis and radius of the second rotation center as the axis and radius of a rotation center of the second rotation guide portion and which engages with the first rotation gear, the bending joint mechanism further includes a second joint section which is provided side by side with the first joint section along the axial direction of the first shaft section and which is disposed forward of the first joint section and which is coupled to the first actuating section, the second joint section includes a second shaft section which has an arc-shaped first rotation guide portion around a first rotation center and which has an axis that intersects at right angles with the axis of the first rotation center, a second actuating section having an arc-shaped second rotation guide portion around a second rotation center, the second rotation guide portion coming in rolling contact with the first rotation guide portion, a second coupling member which is rotatably coupled at a distal end portion thereof to the second rotation center and which is rotatably coupled at a proximal end portion thereof to the first rotation center and a second rod section which is coupled at a distal end portion thereof to a position other than the first rotation center of the second coupling member and which is rotatably coupled at a proximal end portion thereof to the second rotation gear at a position parallel to the axis of the rotation center of the second rotation gear and other than the rotation center and which translates in the axial direction of the second shaft section in response to a driving force, wherein the central axis of the second rotation center of the first actuating section and the central axis of the first rotation center of the second joint section are arranged at skew positions, that is, are arranged to be parallel but not flush, the first rotation gear is rotated by an independent second driving force different from a first driving force that translates the first rod section, whereby the second rotation gear rotates, the second rod section serves as driving force transmitting means to rotate the second coupling member around the first rotation center in response to the rotation of the second rotation gear, the second rotation guide portion of the second joint section turns around the first rotation center of the second joint section along the first rotation guide portion of the second joint section in response to the rotation of the second coupling member, and the second actuating section is bent relative to the second shaft section by the turning of the second rotation guide portion of the second joint section, and the second rod section has an elastic part which is elastically deformable in a longitudinal sectional direction.

According to an aspect of embodiments, a surgical instrument having the bending joint mechanism.

According to an aspect of embodiments, a manipulator having the bending joint mechanism.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a perspective view showing the configuration of essential parts of the joint section of the bending joint mechanism according to the second embodiment;

FIG. 9B is a diagram showing the general configuration of the bending joint mechanism according to the second embodiment, and is a perspective view showing how the joint section is bent;

FIG. 10A is a perspective view showing a first modification of a second drive rod section according to the second embodiment;

FIG. 10B is a perspective view showing a second modification of the second drive rod section according to the second embodiment;

FIG. 10C is a perspective view showing a third modification of the second drive rod section according to the second embodiment;

FIG. 10F is a perspective view showing a sixth modification of the second drive rod section according to the second embodiment;

FIG. 10H is a perspective view showing an eighth modification of the second drive rod section according to the second embodiment;

FIG. 10I is a perspective view showing a ninth modification of the second drive rod section according to the second embodiment;

FIG. 10J is a perspective view showing a tenth modification of the second drive rod section according to the second embodiment.

DETAILED DESCRIPTION OF THE INVENTION

First Embodiment (Configuration)

Figure 1:
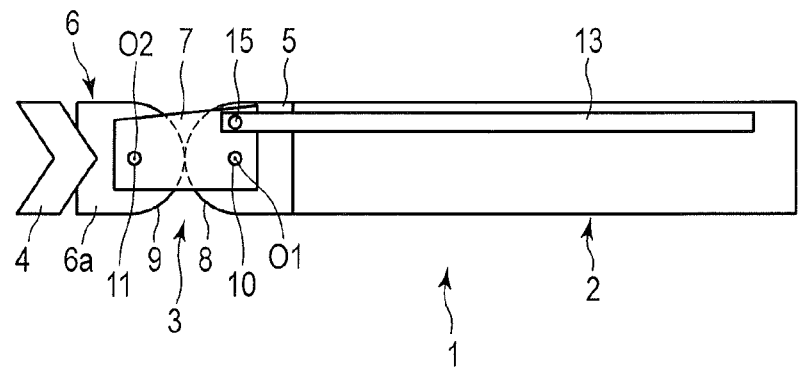
FIG. 1 is a side view showing the overall general configuration of a bending joint mechanism according to a first embodiment of the present invention in which a joint section is kept linear.

FIG. 1, FIG. 2, FIG. 3, FIG. 4, FIG. 5A, and FIG. 5B show the first embodiment of the present invention. FIG. 1 is a side view showing the overall general configuration of a treatment instrument 1 such as a multidegree-of-freedom surgical instrument according to the first embodiment of the present invention. A bending joint mechanism in a joint drive device of the treatment instrument 1 according to the present embodiment is coupled to the distal end of a shaft section 2 and a treatment portion 4 via a joint section 3 having a double joint mechanism. The bending joint mechanism bends the treatment portion 4 relative to the distal end of the shaft section 2 by the joint section 3.

The joint section 3 has the shaft section 2, a support section 5 provided at the distal end portion of the shaft section 2, an actuating section 6 coupled to the treatment portion 4, a drive plate section 7 which functions a coupling member to couple the support section 5 to the actuating section 6, and a drive rod section 13.

The shaft section 2 has an axis that intersects at right angles with the axis of a rotation center (first rotation center) O1 of the support section 5.

Figure 2:
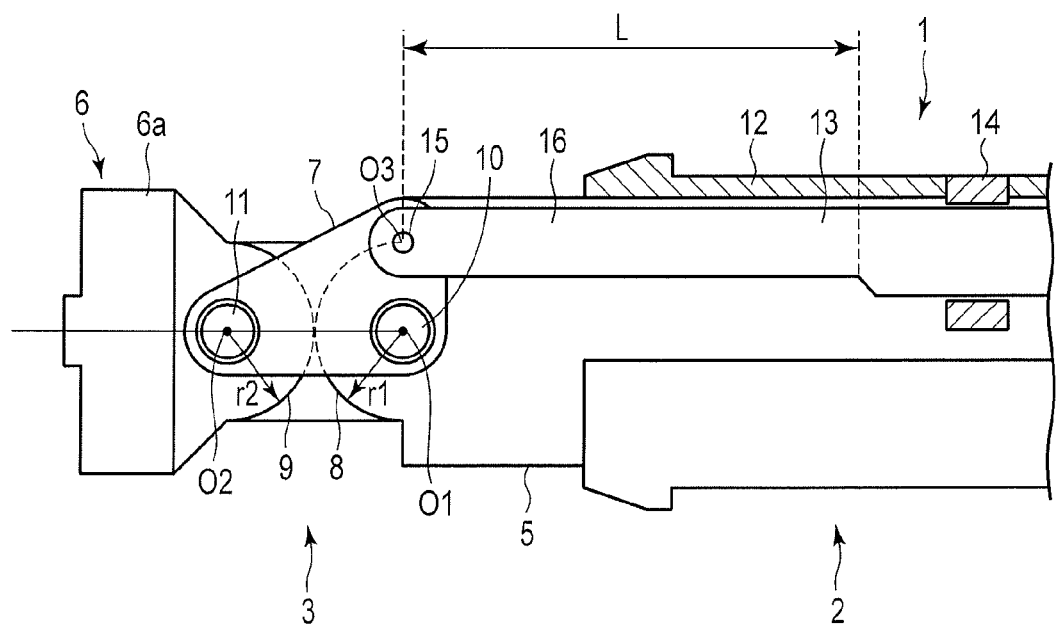
FIG. 2 is a side view showing partly in section how the joint section of the bending joint mechanism according to the first embodiment is kept linear.

As shown in FIG. 2, the proximal end portion of the support section 5 is fixed to the distal end portion of the shaft section 2. A substantially semicircular first guide gear portion (first rotation guide portion) 8 is formed at the distal end portion of the support section 5. The central position of the first guide gear portion 8 is set at the rotation center (first rotation center) O1 of the support section 5. Thus, the shaft section 2 has the semicircular-arc-shaped first guide gear portion (first rotation guide portion) 8 around the rotation center (first rotation center) O1 of the support section 5. The first guide gear portion 8 is semicircular-arc-shaped in the present embodiment, but does not need to be limited thereto. For example, when the bending range of the joint section 3 is small, part of the first guide gear portion 8 has only to be arc-shaped.

The actuating section 6 has an actuating portion main body 6a. The treatment portion 4 is coupled to the distal end portion of the actuating portion main body 6a. A substantially semicircular second guide gear portion (second rotation guide portion) 9 is formed at the proximal end portion of the actuating portion main body 6a. The central position of the second guide gear portion 9 is set at the rotation center (second rotation center) O2 of the actuating section 6. As shown in FIG. 2, the second guide gear portion 9 is in frictional contact with the first guide gear portion 8 in an engaged state. The second guide gear portion 9 rolls relative to (contacts) the first guide gear portion 8 by the drive plate section 7. Thus, the actuating section 6 has the semicircular-arc-shaped second guide gear portion (second rotation guide portion) 9 around the second rotation center O2, the second guide gear portion coming in rolling contact with the first guide gear portion 8. The second guide gear portion 9 is semicircular-arc-shaped in the present embodiment, but does not need to be limited thereto. For example, when the bending range of the joint section 3 is small, part of the second guide gear portion 9 has only to be arc-shaped as is the case with the first guide gear portion 8. As shown in FIG. 2, a radius r1 of the first guide gear portion 8 and a radius r2 of the second guide gear portion 9 are set at a ratio of 1:1.

The first guide gear portion 8 and the second guide gear portion 9 are configured so that their teeth engage in frictional contact with each other in the present embodiment, but are not necessarily limited to this configuration. For example, the first guide gear portion 8 and the second guide gear portion 9 may have a mechanism in which two rotors are in frictional contact with each other and roll without sliding. The rotors mean, for example, two rubber rollers which do not have gears that engage with each other in frictional contact and which have a large frictional force.

Figure 3:
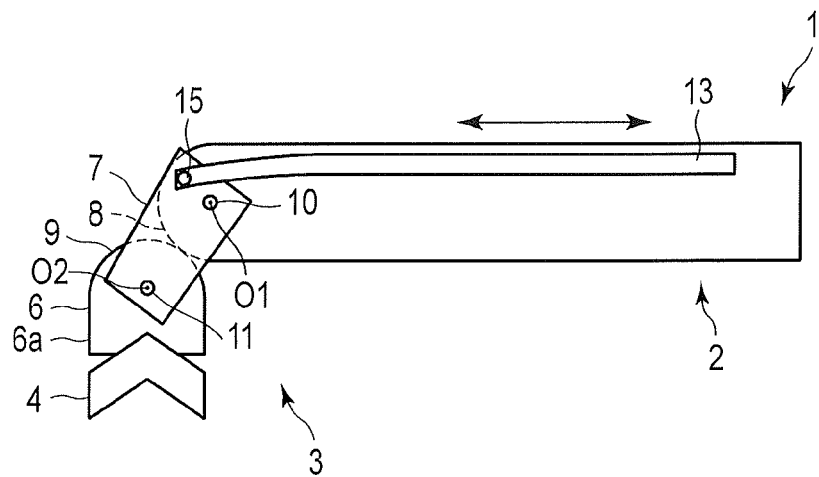
FIG. 3 is a side view showing the overall general configuration of the bending joint mechanism according to the first embodiment of the present invention in which the joint section is bent.

As shown in FIG. 2, the proximal end portion of the drive plate section 7 is coupled to the first rotation center O1 by a first coupling pin 10 rotatably relative to the first rotation center O1. The distal end portion of the drive plate section 7 is coupled to the second rotation center O2 of the actuating section 6 by a second coupling pin 11 rotatably relative to the second rotation center O2. Thus, the drive plate section 7 is rotatably coupled at the distal end portion to the second rotation center O2, and rotatably coupled at the proximal end portion to the first rotation center O1. Accordingly, as shown in FIG. 2 and FIG. 3, the drive plate section 7 keeps the first rotation center O1 and the second rotation center O2 at a distance in the first guide gear portion 8 and the second guide gear portion 9 that come in rolling contact with each other, and roll the second guide gear portion 9 relative to the first guide gear portion 8.

As shown in FIG. 2, the shaft section 2 has a cylindrical housing 12. The support section 5 is coupled to the distal end portion of the housing 12. The drive rod section 13 is translatability provided in the housing 12 of the shaft section 2. A rod receiver 14 which supports the drive rod section 13 translatability in the axial direction of the shaft section 2 is fixed in the housing 12. Under the guidance of the rod receiver 14, the drive rod section 13 translate along the axial direction of the shaft section 2 in response to a driving force transmitted from an unshown driving source.

The distal end portion of the drive rod section 13 is rotatably coupled to a third rotation center O3 by a third coupling pin 15. The third rotation center O3 indicates a position other than the first rotation center O1 at the proximal end portion of the drive plate section 7.

Thus, the drive rod section 13 is supported by the rod receiver 14 translatability relative to the shaft section 2 in the axial direction of the shaft section 2. The drive rod section 13 is also coupled at the distal end portion to the third rotation center O3 which is a position other than the first rotation center O1 at the proximal end portion of the drive plate section 7, and translate in the axial direction of the shaft section 2 in response to the driving force.

Figure 4:
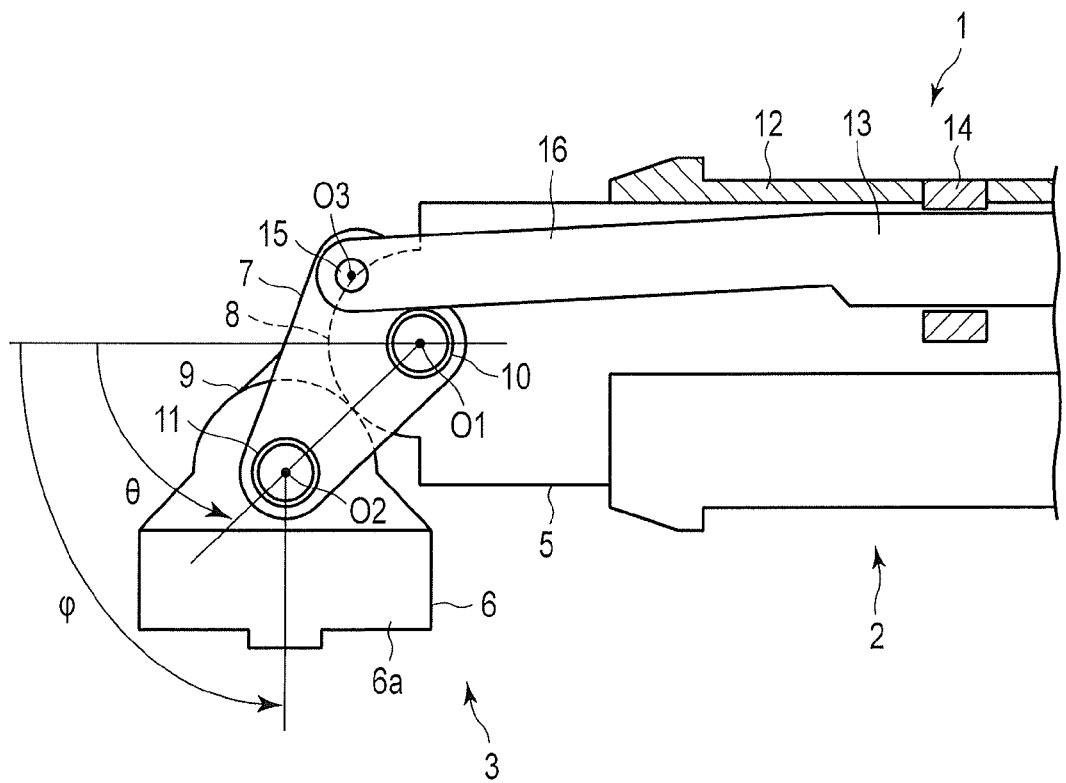
FIG. 4 is a side view showing partly in section how the joint section of the bending joint mechanism according to the first embodiment is bent.

As shown in FIG. 3 and FIG. 4, the drive rod section 13 according to the present embodiment has an elastic member which is elastically deformable in directions other than the axial direction of the shaft section 2. As shown in FIG. 2, the drive rod section 13 has at the distal end portion an elastically deformable portion 16 (elastic part) having a length L of the axial direction. The elastically deformable portion 16 is one-dimensionally elastically deformed in the directions other than the axial direction of the shaft section 2. As the outside diameter of the elastically deformable portion 16 is smaller than the outside diameter of the part of the drive rod section 13 other than the elastically deformable portion 16, the elastically deformable portion 16 is more easily elastically deformed than the part other than the elastically deformable portion 16. Therefore, the sectional area of the drive rod section 13 varies in the axial direction of the drive rod section 13. The drive rod section 13 is made of a metal material such as a stainless steel spring (SUS304CPS).

Alternatively, the drive rod section 13 may be polyether ether ketone resin (PEEK) which is light and which is high in insulation performance and corrosion resistance, a resin spring such as a polyacetal resin (POM resin) or a polycarbonate resin (PC resin), phosphor bronze for a spring, or a shape-memory alloy such as Ni—Ti. Phosphor bronze has high ductility, fatigue resistance, and corrosion resistance, and is annealed at low temperature and is therefore suited to a high-performance spring member. The shape-memory alloy is soft at low temperature, and is rigid at high temperature. The shape-memory alloy is light and is high in corrosion resistance.

In the joint drive device of the treatment instrument 1 according to the present embodiment, as shown in FIG. 3 and FIG. 4, the bending joint mechanism turns the drive plate section 7 around the first rotation center O1 together with the movement in the translating direction of the drive rod section 13, and thus turns the second guide gear portion 9 along the first guide gear portion 8 around the first rotation center O1 together with the movement of the drive plate section 7. As a result, the bending joint mechanism drives the joint section 3, that is, bends the actuating section 6 relative to the shaft section 2.

(Function)

Now, the function of the above configuration is described. In the joint drive device of the treatment instrument 1 according to the present embodiment, in an inactive state, the actuating section 6 and the treatment portion 4 are held in an initial position to be stretched straight along the axial direction of the shaft section 2 as shown in FIG. 1 and FIG. 2.

When the joint section 3 of the treatment instrument 1 is bent from the initial position, the drive rod section 13 translates along the axial direction. For example, if the drive rod section 13 translates forward from the initial position in FIG. 1 and FIG. 2, a press force of the drive rod section 13 acts on the drive plate section 7. At the same time, the drive rod section 13 bends as a beam in an elastic deformation region and also rotates the drive plate section 7 around the first rotation center O1.

In this case, in the joint section 3 (double joint mechanism), the drive plate section 7 turns counterclockwise in FIG. 1 around the first rotation center O1, as shown in FIG. 3 and FIG. 4. Accordingly, the second guide gear portion 9 rolls relative to the first guide gear portion 8 together with the turning of the drive plate section 7. At the same time, the drive plate section 7 turns at an angle corresponding to the ratio between the radius r1 of the first guide gear portion 8 and the radius r2 of the second guide gear portion 9.

$$r2(\phi-\theta)=r1\theta \quad (1)$$

$$\phi=\{(r1+r2)/r2\}\theta \quad (2)$$

wherein θ is the turning angle of the drive plate section 7, and φ is the turning angle of the actuating section 6, as shown in FIG. 4.

For example, φ=2θ when the ratio between the radius r1 of the first guide gear portion 8 and the radius r2 of the second guide gear portion 9 is 1:1 (r1=r2) as in the present embodiment. If the drive plate section 7 turns 45 degrees around the first rotation center O1 as shown in FIG. 4, the second guide gear portion 9 moves 90 degrees relative to the first guide gear portion 8. That is, the bending joint mechanism serves as a speed increasing mechanism so that the angular movement amount of the drive plate section 7 will be smaller than the angular movement amount of the actuating section 6.

Figure 5A:
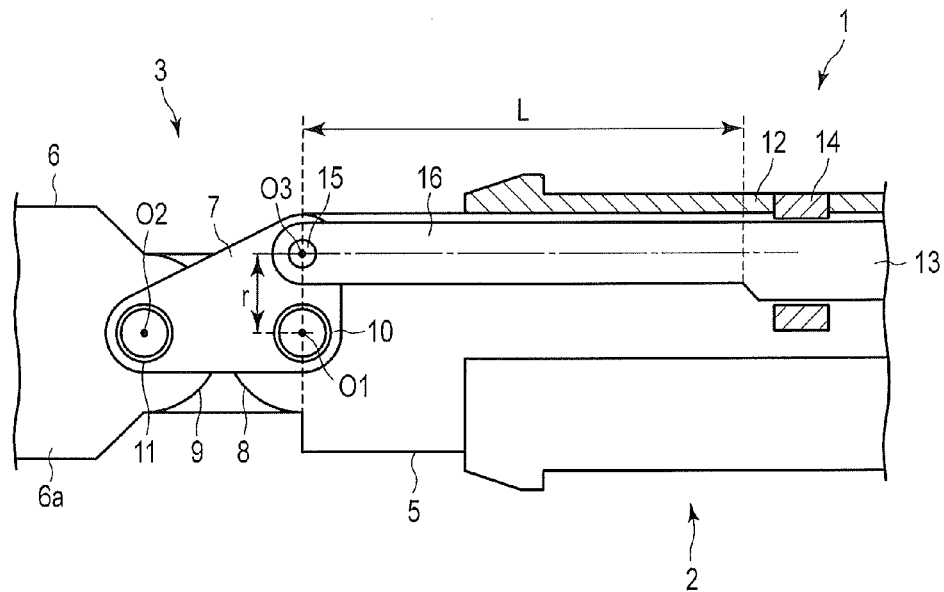
FIG. 5A is a diagram illustrating the function of the joint section of the bending joint mechanism according to the first embodiment, and is a side view showing partly in section how the joint section is kept linear.
Figure 5B:
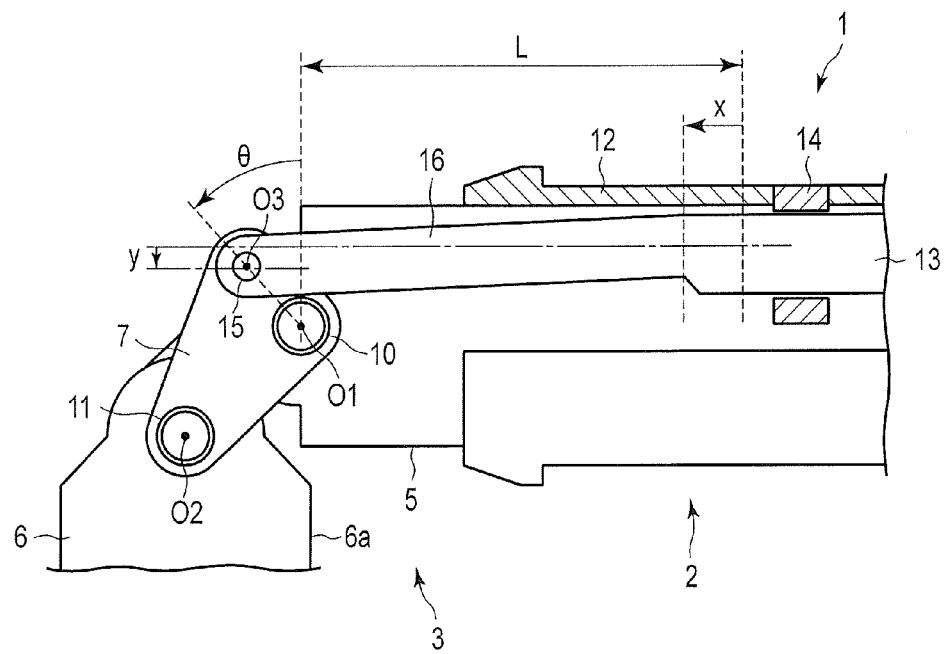
FIG. 5B is a diagram illustrating the function of the joint section of the bending joint mechanism according to the first embodiment, and is a side view showing partly in section how the joint section is bent.

When the drive rod section 13 translates in an x-direction as shown in FIG. 5B from the initial position shown in FIG. 5A and the actuating section 6 turns by the angle φ as shown in FIG. 4 and FIG. 5B, the drive rod section 13 (elastically deformable portion 16) bends as a beam in the elastic deformation region as shown in FIG. 5B. Strain y of the drive rod section 13 in this case is $$y=r(1-\cos(\phi/2)) \quad (3).$$

Therefore, the strain y of the drive rod section 13 is extremely small as shown in Equation (3) when the joint section 3 (double joint mechanism) according to the present embodiment bends, the actuating section 6 turns by the angle φ, and the drive rod section 13 bends. Thus, the strain y can be accommodated within the elastic deformation area of the drive rod section 13.

Advantageous Effects

The configuration described above provides the following advantageous effects. That is, in the joint drive device of the treatment instrument 1 according to the present embodiment, the joint section 3 has two guide members (the first guide gear portion 8 and the second guide gear portion 9) that come into rolling contact with each other, and the drive plate section 7 which keeps the first guide gear portion 8 and the second guide gear portion 9 at a distance and which rolls the second guide gear portion 9 relative to the first guide gear portion 8. In the joint section 3, the drive rod section 13 which permits deformation translates and thereby rotates the drive plate section 7. At the same time, the drive rod section 13 has, at its distal end portion, the elastically deformable portion 16 which is elastically deformed in a direction other than the axial direction of the shaft section 2, and the drive rod section 13 rotates the drive plate section 7 while bending as a beam in the elastic deformation region. Thus, according to the present embodiment, the angular movement amount of the drive plate section 7 can be smaller than the angular movement amount of the actuating section 6, and the joint section 3 which has heretofore been bent by a mechanism such as a parallel link mechanism or a crank mechanism can be controlled by the translating of the drive rod section 13 alone.

Therefore, in the joint drive device of the treatment instrument 1 according to the present embodiment, the shaking of the joint mechanism resulting from shaking caused by a stretched or slackened wire or by the tolerance of mechanical members is reduced, a bending mechanism can be configured by a small number of components even in the case of successive bending joints, and the distal end portion of a treatment instrument such as a multidegree-of-freedom surgical instrument can be accurately positioned.

According to the present embodiment, the drive rod section 13 which rotates the drive plate section 7 functions as a spring, and therefore always provides an elastic force (spring force) to the shaking part produced in the joint section 3 and can reduce the shaking of the joint section 3.

In a conventional mechanism in which the joint section 3 is bent by a parallel link, the joint section 3 bends by a combination of translating movement and rotation movement. Thus, in the conventional mechanism, the movement range is wider, the arrangement of other components is difficult, and the degree of freedom in designing is lower in parts having smaller diameters. However, in the joint drive device of the treatment instrument according to the present embodiment, the drive rod section 13 which turns the drive plate section 7 only translates, so that the drive rod section 13 does not move in its axial section, and the area occupied by the drive rod section 13 is limited to its own area. Thus, according to the present embodiment, the movement area of the drive rod section 13 does not need to occupy a large internal space in the housing 12, and the degree of freedom in designing the internal space of the housing 12 can be higher. As a result, according to the present embodiment, when a packing member is provided in the shaft of the surgical instrument to prevent air leakage during pneumoperitoneum in endoscopic surgery, no movement area in the axial sectional direction of the surgical instrument is needed, and the packing member is easily provided. Moreover, the present embodiment allows for a smaller number of links, lower costs, and a smaller number of assembly processes than in a conventional crank-driven drive mechanism.

First Modification of First Embodiment

Figure 6A:
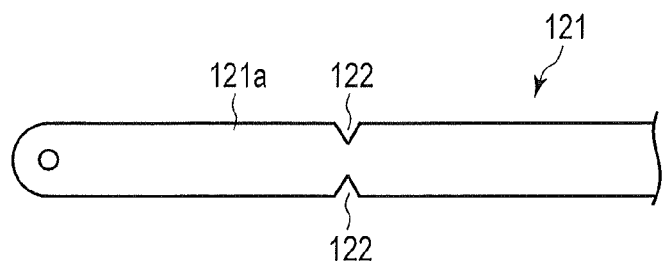
FIG. 6A is a plan view showing a first modification of a drive rod section.

FIG. 6A shows a first modification of the first embodiment. According to the present modification, the shape of the drive rod section 13 according to the first embodiment is changed as follows: A drive rod section 121 according to the present modification has a wedge-shaped cutout portion 122 in a middle portion (elastic part) of a rod body 121a of the drive rod section 121.

According to the present modification, the properties of the spring resilience of the drive rod section 121 can be changed by the cutout portion 122, and the degree of freedom in designing the joint drive device can be enhanced.

Second Modification of First Embodiment

Figure 6B:
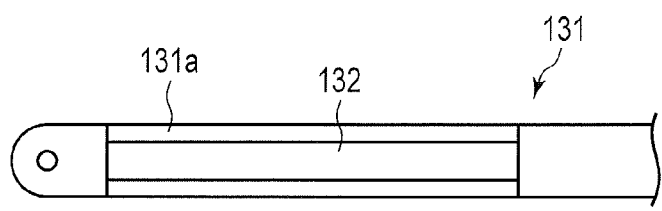
FIG. 6B is a plan view showing a second modification of the drive rod section.

FIG. 6B shows a second modification of the first embodiment. According to the present modification, the shape of the drive rod section 13 according to the first embodiment is changed as follows: A drive rod section 131 according to the present modification has a through-hole portion 132 in the center (elastic part) of a rod body 131a. The through-hole portion 132 is provided along the axial direction of the rod body 131a.

According to the present modification, the properties of the spring resilience of the drive rod section 131 can be changed by the through-hole portion 132, and the degree of freedom the designing the joint drive device can be enhanced.

Third Modification of First Embodiment

Figure 6C:
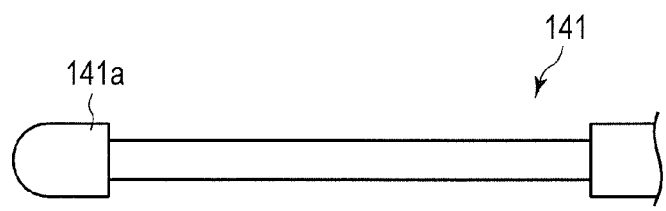
FIG. 6C is a plan view showing a third modification of the drive rod section.

FIG. 6C shows a third modification of the first embodiment. According to the present modification, the shape of the drive rod section 13 according to the first embodiment is changed as follows: A drive rod section 141 according to the present modification is shaped so that a middle portion (elastic part) provided between both end portions of a rod body 141a is smaller in outside diameter than both end portions.

According to the present modification, the properties of the spring resilience of the rod body 141a can be changed, and the degree of freedom in designing the joint drive device can be enhanced.

Fourth Modification of First Embodiment

Figure 6D:
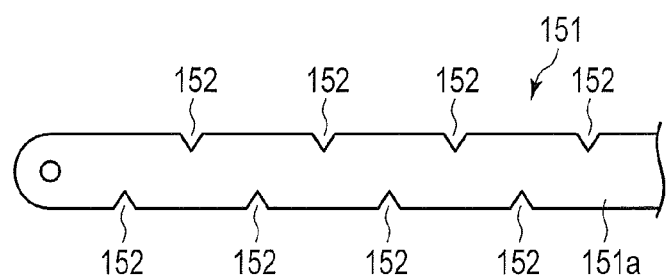
FIG. 6D is a plan view showing a fourth modification of the drive rod section.

FIG. 6D shows a fourth modification of the first embodiment. According to the present modification, the shape of the drive rod section 13 according to the first embodiment is changed as follows: A drive rod section 151 according to the present modification has a plurality of wedge-shaped cutout portions 152 in middle portions (elastic parts) of a rod body 151a. The cutout portions 152 are provided alternately on the upper side and lower side of the drawing.

According to the present modification, the properties of the spring resilience of the drive rod section 151 can be changed by a plurality of cutout portion 152, and the degree of freedom in designing the joint drive device can be enhanced.

Second Embodiment (Configuration)

FIG. 7, FIG. 8, FIG. 9A, and FIG. 9B show the second embodiment of the present invention. According to the present embodiment, a first joint section (first joint section) 22 and a second joint section (second joint section) 23 are provided side by side at the distal end portion of a treatment instrument 21. The first joint section 22 and the second joint section 23 each have a double joint mechanism. The first joint section 22 and the second joint section 23 are substantially similar in configuration to the joint section 3 according to the first embodiment. The second joint section 23 is provided side by side with the first joint section 22 along the axial direction of a shaft section 24 (first shaft section), disposed forward of the first joint section 22, and coupled to an actuating section 6 (first actuating portion) of the first joint section 22.

As shown in FIG. 6, the treatment instrument 21 has the first joint section 22 and the second joint section 23 that are provided between the distal end portion of the shaft section 24 and a treatment portion 25. The first joint section 22 has a first gear 26 which has the same axis and radius of a rotation center as the axis and radius of a rotation center (O1) of a first guide gear portion 8, and a second gear 27 which has the same axis and radius of a rotation center as the axis and radius of a rotation center (O2) of a second guide gear portion 9 and which engages with the first gear 26. The first gear 26 is supported rotatably around the first rotation center O1 via a first rotation shaft 29 in a support portion 28 provided at the distal end portion of the shaft section 24. The second gear 27 is supported rotatably around the second rotation center O2 via a second rotation shaft 30 in the actuating section 6 to come into frictional contact with the first gear 26 in an engaged state. The first rotation center O1 indicates the central position of the first gear 26, and the second rotation center O2 indicates the central position of the second gear 27. A radius r1 of the first gear 26 and a radius r2 of the second gear 27 are set at a ratio of 1:1 in the present embodiment.

A drive rod 32 is translatability provided in a housing 31 of the shaft section 24. A rod receiver shown in FIG. 2 (not shown in FIG. 7) which supports the drive rod 32 translatability in the axial direction of the shaft section 24 is fixed in the housing 31. A drive rod section 13 (first rod) which is not shown in FIG. 7 translate along the axial direction of the shaft section 24 in response to a driving force transmitted from an unshown driving source under the guidance of the unshown rod receiver.

The distal end portion of the drive rod 32 is rotatably coupled to a rotation center O5 via a coupling pin 33. The rotation center O5 indicates the position of part of the first gear 26 other than in the first rotation center O1. Moreover, the drive rod 32 according to the present embodiment is an elastic member which is elastically deformable in directions other than the axial direction of the shaft section 24.

The second joint section 23 has a substantially semicircular-arc-shaped third guide gear portion 34 and a substantially semicircular-arc-shaped fourth guide gear portion 35. The third guide gear portion 34 and the fourth guide gear portion 35 are semicircular-arc-shaped in the present embodiment, but do not need to be limited thereto. For example, when the bending range of the second joint section 23 is small, part of the third guide gear portion 34 and part of the fourth guide gear portion 35 have only to be arc-shaped as in the first embodiment. The third guide gear portion 34 is fixed to an intermediate housing 36. The intermediate housing 36 is provided between the first joint section 22 and the second joint section 23, and constitutes a shaft portion (second shaft portion) of the second joint section 23. The center of the third guide gear portion 34 is set at a rotation center O6 on the intermediate housing 36. The fourth guide gear portion 35 is fixed to the treatment portion 25 to come into frictional contact with the third guide gear portion 34 in an engaged state. The rotation center of the fourth guide gear portion 35 is set on a rotation center O7 of the treatment portion 25. A radius r3 of the third guide gear portion 34 and a radius r4 of the fourth guide gear portion 35 are set at a ratio of 1:1 in the present embodiment. A second drive plate section 42 and a plate section 37 are supported by a third rotation shaft 38 and a fourth rotation shaft 39 rotatably around the rotation center O6 and the rotation center O7.

Here, the third rotation shaft 38 and the fourth rotation shaft 39 which are the rotation shafts of the second joint section 23 are arranged in a direction that intersects at right angles with the first rotation shaft 29 and the second rotation shaft 30 which are the rotation shafts of the first joint section 22. In other words, the central axis of the second rotation center O2 of the first joint section 22 (the actuating section 6) and the central axis of the first rotation center O6 of the second joint section 23 are arranged 90 degrees askew, that is, arranged 90 degrees relative to each other to be parallel but not flush. Thus, the bending direction of the first joint section 22 differs by 90 degrees from the bending direction of the second joint section 23, and the first joint section 22 bends in a direction 90 degrees different from the second joint section 23. Although the bending directions are 90 degrees different from each other in the present embodiment, the angle may vary. In this case, the central axis of the second rotation center O2 of the first joint section 22 (the actuating section 6) and the central axis of the first rotation center O6 of the second joint section 23 are arranged at skew positions corresponding to the bending directions.

A second drive rod (second rod) 40 is disposed in the intermediate housing 36. This second drive rod section 40 is a spring link substantially bent into a crank shape. The proximal end portion of the second drive rod section 40 is coupled to the second gear 27 by a coupling pin 41 rotatably relative to the second gear 27. The coupling pin 41 is disposed parallel to the central axis of the second gear 27. The distal end portion of the second drive rod section 40 is coupled to the second drive plate section 42 by a coupling pin 43 rotatably relative to the second drive plate section 42. The coupling pin 43 is disposed parallel to the central axis (the axis of the rotation center O6) of the third guide gear portion 34. Here, the coupling pin 41 and the coupling pin 43 are disposed to be 90 degrees different from each other in a direction around the axis of the center line of the second drive rod section 40.

The second drive rod section 40 is coupled at the distal end portion to a position of the second drive plate section 42 other than the rotation center O6, and is rotatably coupled at the proximal end portion to a position parallel to the axis of the second rotation center O2 of the second gear 27 and other than the rotation center O2. The second drive rod section 40 translate in the axial direction of the intermediate housing 36 in response to the driving force. The second drive rod section 40 has an elastically deformable portion (elastic part) which is elastically deformable in a longitudinal sectional direction. The elastically deformable portion is two-dimensionally elastically deformed in directions other than the axial direction of the shaft section 2.

How the second drive plate (second coupling member) 42 which is a coupling member is coupled to the third guide gear portion 34 and the fourth guide gear portion 35 is similar to how the drive plate (first coupling member) 7 according to the first embodiment is coupled to the first guide gear portion 8 and the second guide gear portion 9. That is, the third guide gear portion 34 is a first rotation guide portion of the second joint section 23 which functions in the same manner as the first guide gear portion 8. The fourth guide gear portion 35 is a second rotation guide portion of the second joint section 23 which functions in the same manner as the second guide gear portion 9.

An actuating portion (second actuating portion) 46 according to the present embodiment is substantially similar to the actuating section 6 of the first joint section 22.

If the first gear 26 is rotated by an independent second driving force different from a first driving force that translates the drive rod section 13, the second gear 27 rotates. Thus, the second drive rod section 40 functions as driving force transmitting means in response to the rotation of the second gear 27. The second drive rod section 40 then rotates the second drive plate section 42 around the first rotation center (O6) of the second joint section (23). The fourth guide gear portion 35 then turns around the rotation center O6 along the third guide gear portion 34 in response to the rotation of the second drive plate section 42. In consequence, the actuating portion 46 is bent relative to the intermediate housing 36 by the turning of the fourth guide gear portion 35.

(Function)

Figure 9A:
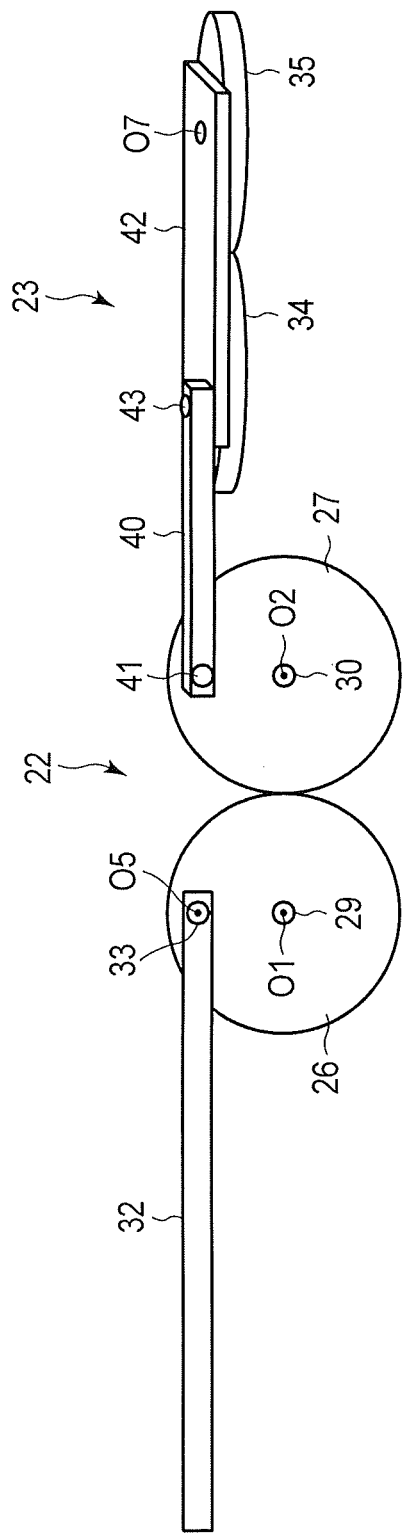
FIG. 9A is a diagram showing the general configuration of the bending joint mechanism according to the second embodiment, and is a perspective view showing how the joint section is kept linear.

Now, the function of the above configuration is described. In the joint drive device of the treatment instrument 21 according to the present embodiment, in an inactive state, the first joint section 22 and the second joint section 23 are held in an initial position to be stretched straight along the axial direction of the shaft section 24 as shown in FIG. 7 and FIG. 9A.

Figure 7:
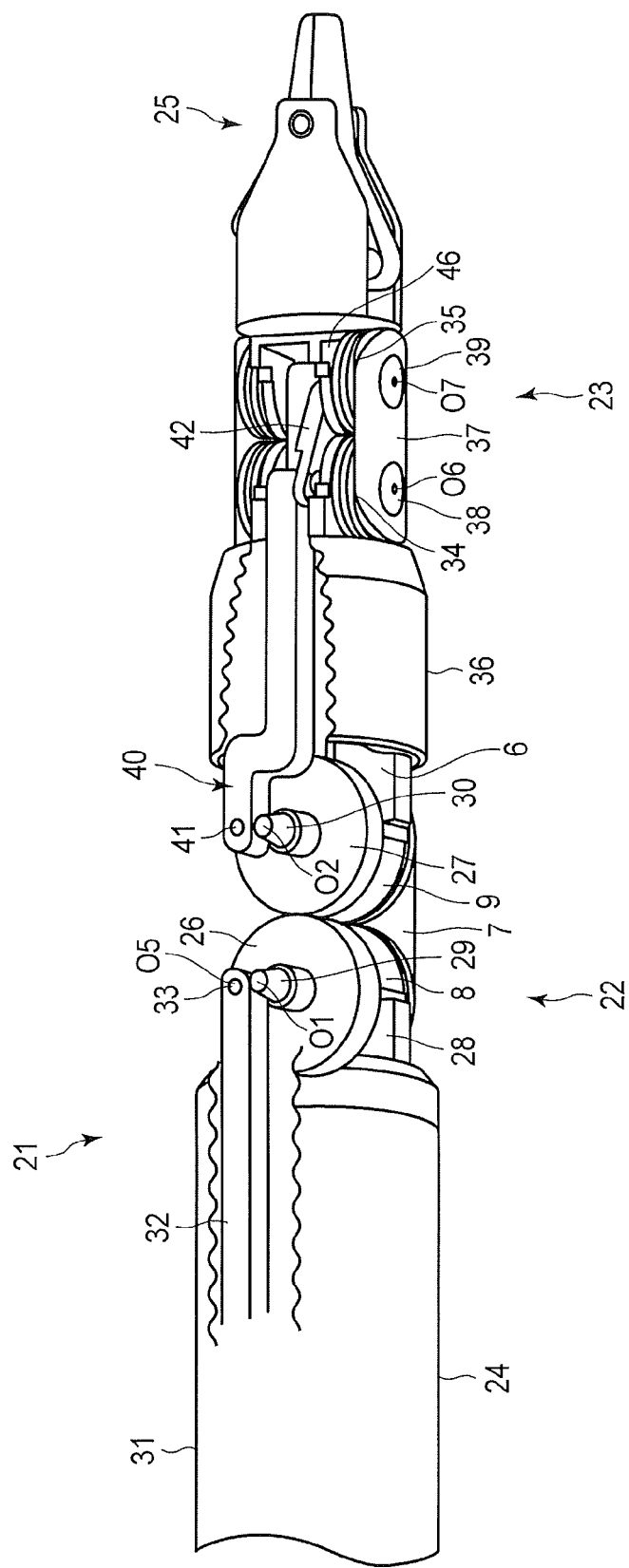
FIG. 7 is a perspective view showing the general configuration of a bending joint mechanism according to a second embodiment of the present invention in which a joint section is kept linear.

When the drive rod section 13 which is not shown in FIG. 7 translates as in the first embodiment, the drive plate section 7 rotates, and the first joint section 22 bends. At the same time, the first gear 26 and the second gear 27 function as guides which simply come into rolling contact with each other in the same manner as the first guide gear portion 8 and the second guide gear portion 9 if the drive rod 32 does not translate. Therefore, the first joint section 22 bends without any influence on the second joint section 23.

If driving force is then transmitted to the drive rod 32 from the unshown driving source, the drive rod 32 translates along the axial direction of the shaft section 24 under the guidance of the unshown rod receiver. As a result, the first gear 26 rotates around the first rotation center O1 via the first rotation shaft 29. At the same time, as shown in FIG. 9B, the second gear 27 engaging with the first gear 26 rotates around the second rotation center O2 via the second rotation shaft 30. As the second gear 27 rotates, the second drive rod section 40 rotates the second drive plate section 42 around the rotation center O6 while being elastically deformed in the axial sectional direction of the intermediate housing 36.

The second joint section 23 bends in the same manner as the movement of the joint section 3 according to the first embodiment together with the movement of the second drive rod section 40.

As long as the drive rod 32 translates and the drive rod section 13 which is not shown in FIG. 7 is fixed, the first joint section 22 is not influenced and not bent even if the second joint section 23 bends. Therefore, the first joint section 22 and the second joint section 23 independently bend.

Advantageous Effects

Thus, according to the present embodiment, the drive rod 32 translates, so that in the first joint section 22, the first gear 26 rotates, the second gear 27 which engages with the first gear 26 rotates, and the second drive rod section 40 translates in the axial sectional direction of the intermediate housing 36 in response to the rotation of the second gear 27. At the same time, the second drive rod section 40 can, while bending as a beam in the elastic deformation region in the axial sectional direction of the intermediate housing 36, rotate the second drive plate section 42 of the second joint section 23 as in the first embodiment, and bend the second joint section 23. Moreover, while bending as a beam in the elastic deformation region, the drive rod section 13 can rotate the first guide gear portion 8 of the first joint section 22 as described above, and can bend the first joint section 22.

Thus, according to the present embodiment, the second joint section 23 can also be controlled by the translating of the second drive rod section 40 as in the first embodiment.

According to the present embodiment, the rotation shaft (the third rotation shaft 38 and the fourth rotation shaft 39) in the second joint section 23 is disposed in a direction that intersects at right angles with the rotation shaft (the first rotation shaft 29 and the second rotation shaft 30) in the first joint section 22. Thus, according to the present embodiment, in addition to the advantageous effects according to the first embodiment, the first joint section 22 and the second joint section 23 can be bent in directions 90 degrees different from each other. Moreover, according to the present embodiment, the first joint section 22 and the second joint section 23 are bent by the drive rod 32 and the second drive rod section 40 which are elastically deformed in the longitudinal sectional direction and which are less easily elastically deformed in the longitudinal direction than in the longitudinal sectional direction. In this way, assembly shaking is constrained and reduced by spring effects, and the number of necessary components can be reduced.

Although the first gear 26 is rotated by the drive rod 32 in the present embodiment, this is not a limitation. For example, a pulley may be provided in the first gear 26, and a driving force transmitting member such as a belt or a wire is connected to the pulley so that the first gear 26 is rotated by the driving force transmitting member. Alternatively, a link may rotate the first gear 26. As described above, the member for rotating the first gear 26 is not limited to the drive rod 32.

Although the first joint section 22 and the second joint section 23 are provided at the distal end portion of the treatment instrument 21 in the present embodiment, the first joint section 22 and the second joint section 23 may be provided in an intermediate portion of the treatment instrument 21. Moreover, a plurality of joint sections having the first joint section 22 and the second joint section 23 that are arranged in parallel may be provided side by side.

In the present embodiment, a first drive rod for bending the first joint section 22 is preferably the elastically deformable drive rod section 13. However, a first drive rod of a member which is not elastically deformed may be used to bend the first joint section 22.

First Modification of Second Embodiment

FIG. 10A shows a first modification of the second drive rod section 40 according to the second embodiment of the present invention. According to the present modification, the shape of the spring link of the second drive rod section 40 according to the second embodiment is changed as follows: A drive rod section 51 according to the present modification has a rod body 51a which is rectangular in section. The rod body 51a is provided with a first through-hole portion 52 and a second through-hole portion 53 that constitute an elastic part. The first through-hole portion 52 is disposed to perforate between one pair of opposite side surfaces (e.g., the upper surface and the lower surface) of the rod body 51a. The second through-hole portion 53 is disposed to perforate between the other pair of opposite side surfaces (e.g., the left surface and the right surface) of the rod body 51a. The first through-hole portion 52 and the second through-hole portion 53 are long hole portions extending along the axial direction of the drive rod section 51.

A coupling pin 54 at the proximal end portion of the drive rod section 51 and a coupling pin 55 at the distal end portion of the drive rod section 51 are disposed at a rotation angle of 90 degrees to each other in a direction around the axis of the center line of the drive rod section 51.

Thus, the spring resilience of the drive rod section 51 according to the present modification can be changed by adjustment of the sizes of the first through-hole portion 52 and the second through-hole portion 53, and in addition to the advantageous effects according to the second embodiment, the degree of freedom in designing the joint drive device can be enhanced.

Second Modification of Second Embodiment

FIG. 10B shows a second modification of the second drive rod section 40 according to the second embodiment. According to the present modification, the shape of the spring link of the second drive rod section 40 according to the second embodiment is changed as follows: A drive rod section 61 according to the present modification has a rod body 61a which is rectangular in section. The rod body 61a is provided with a first through-hole portion 62 and a second through-hole portion 63 that constitute an elastic part. The first through-hole portion 62 is disposed to perforate between one pair of opposite side surfaces (e.g., the upper surface and the lower surface) of the rod body 62a. The second through-hole portion 63 is disposed to perforate between the other pair of opposite side surfaces (e.g., the left surface and the right surface) of the rod body 62a. According to the present modification, the first through-hole portion 62 is disposed along the axial direction of the drive rod section 61, and is a short hole portion which is substantially half the rod body 61a in length. The second through-hole portion 63 is disposed along the axial direction of the drive rod section 61, and is a long hole portion having a length which is nearly the entire length of the rod body 61a.

A coupling pin 64 at the proximal end portion of the drive rod section 61 and a coupling pin 65 at the distal end portion of the drive rod section 61 are disposed at a rotation angle of 90 degrees to each other in a direction around the axis of the center line of the drive rod section 61.

Thus, in the drive rod section 61 according to the present modification, the spring resilience, bending position, and bending balance of the drive rod section 61 can be further changed by the adjustment of the shapes (width, length, position) of the first through-hole portion 62 and the second through-hole portion 63, and in addition to the advantageous effects according to the second embodiment, the degree of freedom in designing the joint drive device can be enhanced.

Third Modification of Second Embodiment

FIG. 10C shows a third modification of the second drive rod section 40 according to the second embodiment. According to the present modification, the shape of the spring link of the second drive rod section 40 according to the second embodiment is changed as follows: A drive rod section 71 according to the present modification has a rod body 71a which is rectangular in section. The rod body 71a is provided with first through-hole portions 72a and 72b and second through-hole portions 73a and 73b that constitute an elastic part. The first through-hole portions 72a and 72b are disposed to perforate between one pair of opposite side surfaces (e.g., the upper surface and the lower surface) of the rod body 71a. The second through-hole portions 73a and 73b are disposed to perforate between the other pair of opposite side surfaces (e.g., the left surface and the right surface) of the rod body 71a. The first through-hole portions 72a and 72b and the second through-hole portions 73a and 73b are long hole portions extending along the axial direction of the drive rod section 71. The first through-hole portions 72a and 72b are provided side by side in a direction (width direction of the drive rod section 71) perpendicular to the axial direction of a drive rod section 181. The second through-hole portions 73a and 73b are provided side by side in a direction (width direction of the drive rod section 71) perpendicular to the axial direction of the drive rod section 71.

A coupling pin 74 at the proximal end portion of the drive rod section 71 and a coupling pin 75 at the distal end portion of the drive rod section 71 are disposed at a rotation angle of 90 degrees to each other in a direction around the axis of the center line of the drive rod section 71.

Thus, the spring resilience of the drive rod section 71 according to the present modification can be changed by adjustment of the sizes of the first through-hole portions 72a and 72b and the second through-hole portions 73a and 73b, and in addition to the advantageous effects according to the second embodiment, the degree of freedom in designing the joint drive device can be enhanced.

Fourth Modification of Second Embodiment

Figure 10D:
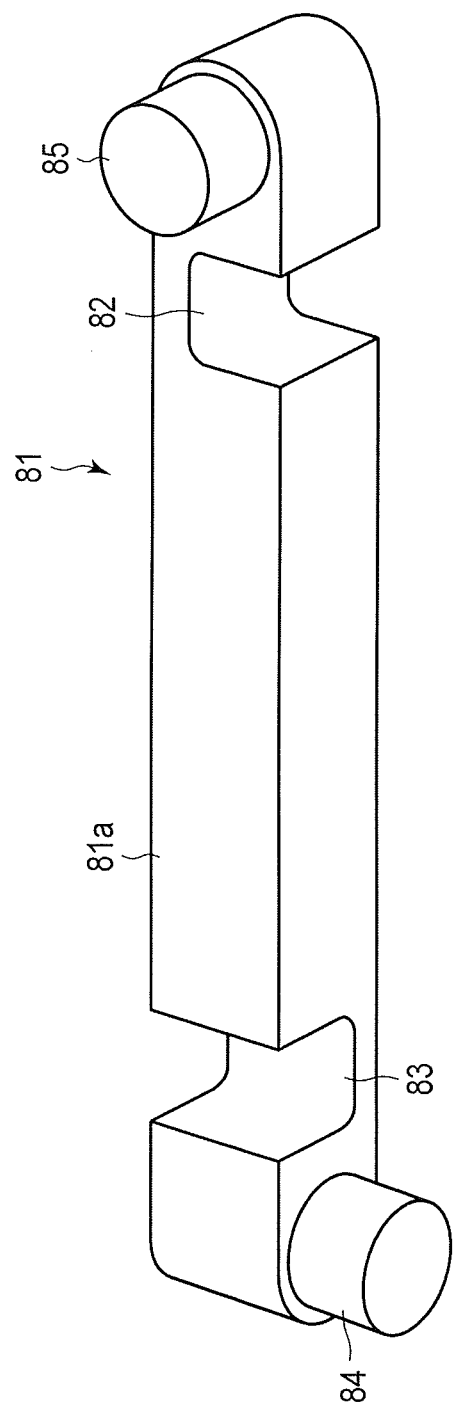
FIG. 10D is a perspective view showing a fourth modification of the second drive rod section according to the second embodiment.

FIG. 10D shows a fourth modification of the second drive rod section 40 according to the second embodiment. According to the present modification, the shape of the spring link of the second drive rod section 40 according to the second embodiment is changed as follows: A drive rod section 81 according to the present modification has a rod body 81a which is rectangular in section. The rod body 81a is provided with a first through-trench portion 82 and a second through-trench portion 83 that constitutes an elastic part. The first through-trench portion 82 is disposed to perforate between one pair of opposite side surfaces (e.g., the upper surface and the lower surface) of the rod body 81a. The second through-trench portion 83 is disposed to perforate between the other pair of opposite side surfaces (e.g., the left surface and the right surface) of the rod body 81a. The first through-trench portion 82 is disposed on the distal end portion side of the drive rod section 81, and the second through-trench portion 83 is disposed on the proximal end portion side of the drive rod section 81.

A coupling pin 84 at the proximal end portion of the drive rod section 81 and a coupling pin 85 at the distal end portion of the drive rod section 81 are disposed at a rotation angle of 90 degrees to each other in a direction around the axis of the center line of the drive rod section 81.

Thus, in the drive rod section 81 according to the present modification, the spring resilience of the drive rod section 81 can be changed by adjustment of the sizes of the first through-trench portion 82 and the second through-trench portion 83, and in addition to the advantageous effects according to the second embodiment, the degree of freedom in designing the joint drive device can be enhanced.

Fifth Modification of Second Embodiment

Figure 10E:
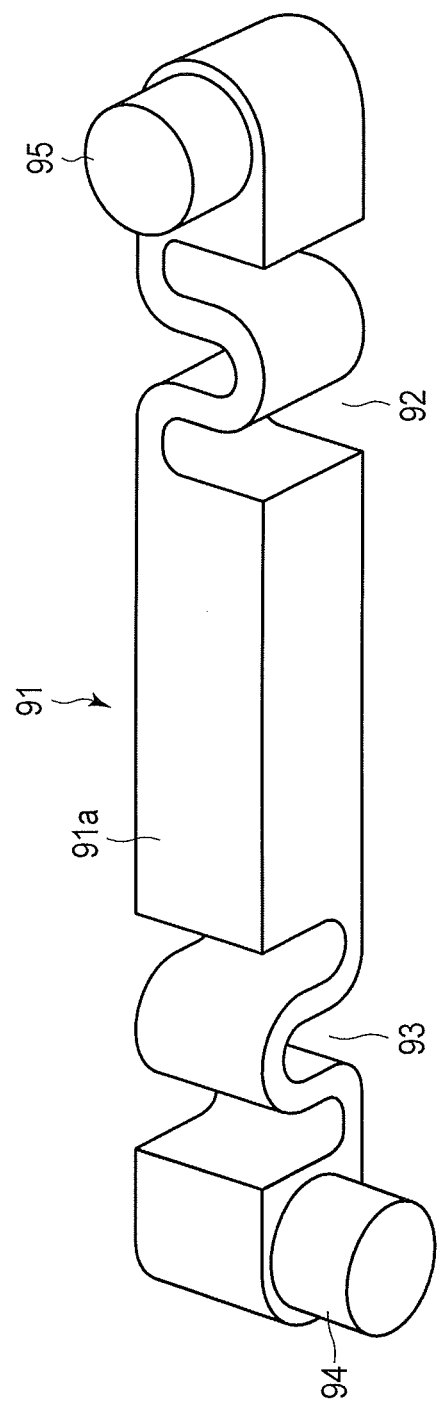
FIG. 10E is a perspective view showing a fifth modification of the second drive rod section according to the second embodiment.

FIG. 10E shows a fifth modification of the second drive rod section 40 according to the second embodiment. According to the present modification, the shape of the spring link of the second drive rod section 40 according to the second embodiment is changed as follows: A drive rod section 91 according to the present modification has a rod body 91a which is rectangular in section. The rod body 91a is provided with a corrugated first leaf spring 92 and a corrugated second leaf spring 93 that constitute an elastic part. The corrugated first leaf spring 92 is disposed to perforate between one pair of opposite side surfaces (e.g., the upper surface and the lower surface) of the rod body 92a. The second leaf spring 93 is disposed to perforate between the other pair of opposite side surfaces (e.g., the left surface and the right surface) of the rod body 92a. The first leaf spring 92 is disposed on the distal end portion side of the drive rod section 91, and the second leaf spring 93 is disposed on the proximal end portion side of the drive rod section 91.

A coupling pin 94 at the proximal end portion of the drive rod section 91 and a coupling pin 95 at the distal end portion of the drive rod section 91 are disposed at a rotation angle of 90 degrees to each other in a direction around the axis of the center line of the drive rod section 91.

Thus, in the drive rod section 91 according to the present modification, the spring resilience of the drive rod section 91 can be changed by adjustment of the sizes of the first leaf spring 92 and the second leaf spring 93, and in addition to the advantageous effects according to the second embodiment, the degree of freedom in designing the joint drive device can be enhanced.

Sixth Modification of Second Embodiment

FIG. 10F shows a sixth modification of the second drive rod section 40 according to the second embodiment. According to the present modification, the shape of the spring link of the second drive rod section 40 according to the second embodiment is changed as follows: A drive rod section 101 according to the present modification has a substantially columnar rod body 101a. The section of the rod body 101a is circular. The cross sectional area of the rod body 101a varies in the axial direction of the rod. That is, the rod body 101a constitutes an elastic part. For example, the rod body 101a is small in cross sectional area in the central portion, and increases in cross sectional area from the central portion toward both end portion sides. Although the rod body 101a is columnar in the present modification, the rod body 101a may have a polygonal and columnar shape and is not particularly limited in shape.

A coupling pin 104 at the proximal end portion of the drive rod section 101 and a coupling pin 105 at the distal end portion of the drive rod section 101 are disposed at a rotation angle of 90 degrees to each other in a direction around the axis of the center line of the drive rod section 101.

Thus, in the drive rod section 101 according to the present modification, the cross sectional area of the rod body 101a varies in the axial direction of the rod, so that the spring resilience of the drive rod section 101 can be changed by adjustment of the shape of the rod body 101a. In addition to the advantageous effects according to the second embodiment, the degree of freedom in designing the joint drive device can be enhanced.

Seventh Modification of Second Embodiment

Figure 10G:
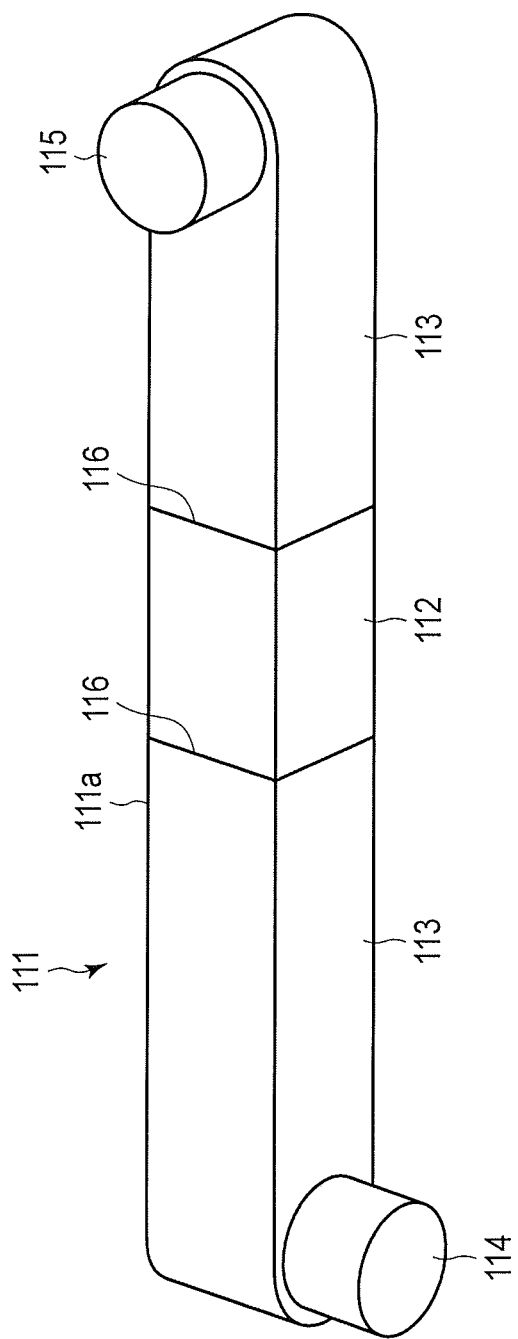
FIG. 10G is a perspective view showing a seventh modification of the second drive rod section according to the second embodiment.

FIG. 10G shows a seventh modification of the second drive rod section 40 according to the second embodiment. According to the present modification, the shape of the spring link of the second drive rod section 40 according to the second embodiment is changed as follows: A drive rod section 111 according to the present modification has a rod body 111a which is rectangular in section. The rod body 111a is constituted of a first block member 112 and a second block member 113 that are different in material. The first block member 112 is disposed in the central portion of the rod body 111a in the axial direction of the rod body 111a, and made of a material having a high spring property (Young's modulus). The second block member 113 is disposed on both portion sides of the first block member 112 in the axial direction of the rod body 111a, and made of a material lower in spring property (Young's modulus) than the first block member 112. The first block member 112 and the second block member 113 are fixed (joined) to each other by a joint 116 such as welding. That is, the rod body 111a constitutes an elastic part. Thus, the Young's modulus of the drive rod section 111 varies in the axial direction of the drive rod section 111. Moreover, the rod body 111a is dividable into a plurality of components (the first block member 112 and the second block member 113) different in material. Although the rod body 111a is rectangular in section in the present modification, the rod body 111a may be polygonal or circular and is not particularly limited in shape.

A coupling pin 114 at the proximal end portion of the drive rod section 111 and a coupling pin 115 at the distal end portion of the drive rod section 111 are disposed at a rotation angle of 90 degrees to each other in a direction around the axis of the center line of the drive rod section 111.

Thus, in the present modification, the rod body 111a is constituted of the first block member 112 and the second block member 113. Consequently, in the present modification, the Young's modulus of the drive rod section 111 can vary in the axial direction of the drive rod section 111, and in addition to the advantageous effects according to the second embodiment, the degree of freedom in designing the joint drive device can be enhanced.

Eighth Modification of Second Embodiment

FIG. 10H shows an eighth modification of the second drive rod section 40 according to the second embodiment. According to the present modification, the shape of the spring link of the second drive rod section 40 according to the second embodiment is changed as follows: A drive rod section 161 according to the present modification has a plate-shaped rod body 161a. The rod body 161a is twisted in a direction around the axis of the center line of the rod body 161a substantially from the central portion in the longitudinal direction of the rod body 161a. Here, the cross sectional area of the rod body 161a is the same over the entire length in the longitudinal direction of the drive rod section 161. That is, the rod body 161a constitutes an elastic part.

A coupling pin 163 at the proximal end portion of the drive rod section 161 and a coupling pin 164 at the distal end portion of the drive rod section 161 are disposed at a rotation angle of 90 degrees to each other in a direction around the axis of the center line of the drive rod section 161.

Thus, in the present modification, the drive rod section 161 can be elastically deformed two-dimensionally in directions other than the axial direction by the twisted rod body 161a. Moreover, in the present modification, the spring resilience of the drive rod section 161 can be changed by the use of the drive rod section 161, and in addition to the advantageous effects according to the second embodiment, the degree of freedom in designing the joint drive device can be enhanced.

Ninth Modification of Second Embodiment

FIG. 10I shows a ninth modification of the second drive rod section 40 according to the second embodiment. According to the present modification, the shape of the spring link of the second drive rod section 40 according to the second embodiment is changed as follows: In a drive rod section 171 according to the present modification, a coupling pin 172 at a proximal end portion 171a of the drive rod section 171 and a coupling pin 173 at a distal end portion 171b of the drive rod section 171 are disposed at a rotation angle of 90 degrees to each other in a direction around the axis of the center line of the drive rod section 171. Moreover, the drive rod section 171 according to the present modification includes a link 174 which is disposed between the proximal end portion 171a and the distal end portion 171b and which has a truss structure.

Thus, in the present modification, the drive rod section 171 can be elastically deformed two-dimensionally in directions other than the axial direction of the drive rod section 171 by the link 174 having the truss structure. That is, the link 174 constitutes an elastic part. Moreover, in the present modification, the spring resilience of the drive rod section 171 can be changed by the use of the drive rod section 171, and in addition to the advantageous effects according to the second embodiment, the degree of freedom in designing the joint drive device can be enhanced.

Tenth Modification of Second Embodiment

FIG. 10J shows a tenth modification of the second drive rod section 40 according to the second embodiment. According to the present modification, the shape of the spring link of the second drive rod section 40 according to the second embodiment is changed as follows: A drive rod section 181 according to the present modification has a rod body 181a which is rectangular in section. The rod body 181a has a plurality of first through-hole portions 182 and a plurality of second through-hole portions 183 that constitute an elastic part. The first through-hole portions 182 are disposed to perforate between one pair of opposite side surfaces (e.g., the upper surface and the lower surface) of the rod body 181a. The second through-hole portions 183 are disposed to perforate between the other pair of opposite side surfaces (e.g., the left surface and the right surface) of the rod body 181a. The first through-hole portions 182 and the second through-hole portions 183 are short holes extending along the axial direction of the drive rod section 181. A plurality of first through-hole portions 182 are provided along the axial direction of the drive rod section 181. A plurality of second through-hole portions 183 are provided along the axial direction of the drive rod section 181.

A coupling pin 184 at the proximal end portion of the drive rod section 181 and a coupling pin 185 at the distal end portion of the drive rod section 181 are disposed at a rotation angle of 90 degrees to each other in a direction around the axis of the center line of the drive rod section 181.

Thus, in the present modification, the first through-hole portions 182 are formed as a plurality of short holes, and the second through-hole portions 183 are formed as a plurality of short hole portions, so that the drive rod section 181 can be difficult to buckle. Moreover, in the present modification, in addition to the advantageous effects according to the second embodiment, the degree of freedom in designing the joint drive device can be enhanced by the use of the drive rod section 181.

Third Embodiment (Configuration)

Figure 11:
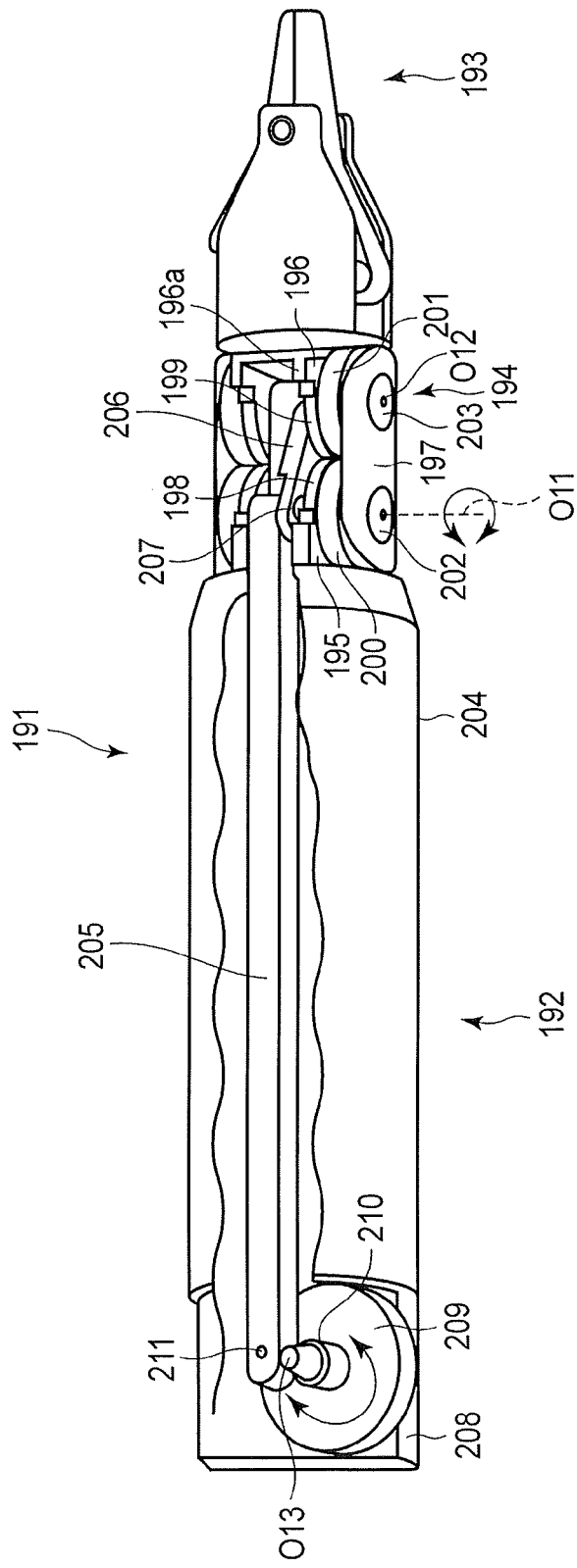
FIG. 11 is a perspective view showing the general configuration of a bending joint mechanism according to a third embodiment of the present invention in which a joint section is kept linear.

FIG. 11 shows a treatment instrument 191 according to the third embodiment of the present invention. The treatment instrument 191 according to the present embodiment has a joint section 194 provided between the distal end portion of a shaft section 192 and a treatment portion 193. The joint section 194 is substantially similar in configuration to the joint section 3.

The joint section 194 has the shaft section 192, a support section 195 provided at the distal end portion of the shaft section 192, an actuating section 196 coupled to the treatment portion 193, a plate section 197 which is a coupling member for coupling the support section 195 to the actuating section 196, a drive plate section 206, and a drive rod section 205.

The shaft section 192 has an axis that intersects at right angles with the axis of a rotation center (first rotation center) 011 of the support section 195.

The proximal end portion of the support section 195 is fixed to the distal end portion of the shaft section 192. A substantially semicircular-arc-shaped first guide gear portion (first rotation guide portion) 198 is formed at the distal end portion of the support section 195. The central position of the first guide gear portion 198 is set at the rotation center (first rotation center) 011 of the support section 195. Thus, the shaft section 192 has the semicircular-arc-shaped first guide gear portion (first rotation guide portion) 198 around the rotation center (first rotation center) O11 of the support section 195. The first guide gear portion 198 is semicircular-arc-shaped in the present embodiment, but does not need to be limited to this shape. For example, when the bending range of the joint section 194 is small, part of the first guide gear portion 198 has only to be arc-shaped.

The actuating section 196 has an actuating portion main body 196a. The treatment portion 193 is coupled to the distal end portion of the actuating portion main body 196a. A substantially semicircular-arc-shaped second guide gear portion (second rotation guide portion) 199 is formed at the proximal end portion of the actuating portion main body 196a. The central position of the second guide gear portion 199 is set at a rotation center (second rotation center) O12 of the actuating section 196. The second guide gear portion 199 is in frictional contact with the first guide gear portion 198 in an engaged state. The second guide gear portion 199 rolls relative to (contacts) the first guide gear portion 198 by the drive plate section 206. Thus, the actuating section 196 has the semicircular-arc-shaped second guide gear portion (second rotation guide portion) 199 around the second rotation center O12, the second guide gear portion 199 coming in rolling contact with the first guide gear portion 198. The second guide gear portion 199 is semicircular-arc-shaped in the present embodiment, but does not need to be limited to this shape. For example, when the bending range of the joint section 194 is small, part of the second guide gear portion 199 has only to be arc-shaped as is the case with the first guide gear portion 198. A radius r1 of the first guide gear portion 198 and a radius r2 of the second guide gear portion 199 are set at a ratio of 1:1.

Furthermore, the joint section 194 has a first gear 200 having the same axis and radius as the axis (the axis of the first rotation center O11) and radius of the first guide gear portion 198, and a second gear 201 which has the same axis and radius as the axis (the axis of the second rotation center O12) radius of the second guide gear portion 199. The first gear 200 is supported rotatably around the first rotation center O11 via a first rotation shaft 202 in the support section 195 provided at the distal end portion of the shaft section 192. The second gear 201 is supported rotatably around the second rotation center O12 via a second rotation shaft section 203 to come into frictional contact with the first gear 200 in an engaged state. The first rotation center O11 indicates the central position of the first gear 200, and the second rotation center O12 indicates the central position of the second gear 201. A radius r1 of the first gear 200 and a radius r2 of the second gear 201 are set at a ratio of 1:1 in the present embodiment.

The proximal end portion of the drive plate section 206 is coupled to the first rotation center O11 by an unshown first coupling pin rotatably relative to the first rotation center O11. The distal end portion of the drive plate section 206 is coupled to the second rotation center O12 of the actuating section 196 by an unshown second coupling pin rotatably relative to the second rotation center O12. Thus, the drive plate section 206 is rotatably coupled at the distal end portion to the second rotation center O12, and rotatably coupled at the proximal end portion to the first rotation center O11. Accordingly, in the same manner as the drive plate section 7, the drive plate section 206 keeps the first rotation center O11 and the second rotation center O12 at a distance in the first guide gear portion 198 and the second guide gear portion 199 that come in rolling contact with each other, and roll the second guide gear portion 199 relative to the first guide gear portion 198. That is, the drive plate section 206 functions as a coupling member, in the same manner as the drive plate section 7.

The drive rod section 205 is translatability provided in a housing 204 of the shaft section 192. A rod receiver shown in FIG. 2 (not shown in FIG. 11) which supports the drive rod section 205 translatability in the axial direction of the shaft section 192 may be fixed in the housing 204. The drive rod section 205 translate along the axial direction of the shaft section 192 in response to the driving force transmitted from an unshown driving source under the guidance of the unshown rod receiver. Thus, the drive rod section 205 is supported by the unshown rod receiver translatability relative to the shaft section 192 in the axial direction of the shaft section 192. The drive rod section 205 is also coupled at the distal end portion to a position other than the first rotation center O11 at the proximal end portion of the drive plate section 206, and translate in the axial direction of the shaft section 192 in response to the driving force. The drive rod section 205 according to the present embodiment is an elastic member which is elastically deformed two-dimensionally in directions other than the axial direction of the shaft section 192. That is, substantially the entire length of the drive rod section 205 constitutes an elastic part. The distal end portion of the drive rod section 205 is coupled to the drive plate section 206 by a coupling pin 207 rotatably relative to the drive plate section 206. The coupling pin 207 is disposed parallel to a first rotation axis 202 of the first guide gear portion 198.

A base plate section 208 is disposed at the proximal end portion of the shaft section 192. The direction that intersects at right angles with the planar direction of the base plate section 208 intersects at right angles with the axial direction of the first rotation center O11 and the axial direction of the shaft section 192. A drive gear 209 is supported on the base plate section 208 by a third rotation shaft 210. The drive gear 209 is rotatable relative to the base plate section 208 around a rotation center O13 of the third rotation shaft 210. The axial direction of the rotation center O13 is substantially parallel to the direction that intersects at right angles with the planar direction of the base plate section 208.

The proximal end portion of the drive rod section 205 is rotatably coupled to the drive gear 209 by a coupling pin 211. The coupling pin 211 is disposed parallel to the third rotation shaft 210. Here, the coupling pin 211 and the coupling pin 207 are disposed at a rotation angle of 90 degrees to each other in a direction around the axis of the center line of the drive rod section 205.

How the drive plate section 206 is coupled to the first guide gear portion 198 and the second guide gear portion 199 is set to be similar to how the drive plate section 7 according to the first embodiment is coupled to the first guide gear portion 8 and the second guide gear portion 9. That is, the first guide gear portion 198 is a first rotation guide portion of the joint section 194, and the second guide gear portion 199 is a second rotation guide portion of the joint section 194.

In the joint drive device of the treatment instrument 191 according to the present embodiment, the bending joint mechanism turns the drive plate section 206 around the position of the first rotation center O11 together with the movement in the translating direction of the drive rod section 205, and thus turns the second guide gear portion 199 along the first guide gear portion 198 around the first rotation center O11 together with the movement of the drive plate section 206. As a result, the bending joint mechanism drives the joint section 194, that is, bends the actuating section 196 relative to the shaft section 192.

(Function)

Now, the function of the above configuration is described. In the joint drive device of the treatment instrument 191 according to the present embodiment, in an inactive state, the joint section 194 is held in an initial position to be stretched straight along the axial direction of the shaft section 192 as shown in FIG. 11.

When the joint section 194 is bent, the drive gear 209 rotates around the third rotation shaft 210. At the same time, the drive rod section 205 rotates the drive plate section 206 via the coupling pin 207 around the first rotation center O11 via the first rotation shaft section 202 while being elastically deformed in the axial sectional direction of the housing 204 of the shaft section 192.

The joint section 194 bends in the same manner as the joint section 3 according to the first embodiment together with the movement of the drive rod section 205.

Advantageous Effects

Thus, according to the present embodiment, the first rotation shaft section 202 and the second rotation shaft section 203 which are two rotation shafts of the joint section 194 intersect at right angles with the third rotation shaft 210. Consequently, according to the present embodiment, in addition the advantageous effects according to the first embodiment, the joint section 194 can be bent in a direction 90 degrees different from the planar direction of the drive gear 209. Moreover, according to the present embodiment, the joint section 194 is bent by the drive rod section 205 which is two-dimensionally elastically deformed in the longitudinal sectional direction and which is less easily deformed in the longitudinal direction than the elastic deformation in the sectional direction. In this way, according to the present embodiment, the elastic force (spring force) is supplied to assembly shaking generated in the joint section 194, so that the shaking can be reduced, and a necessary number of components can be reduced.

Furthermore, the present invention is not limited to the embodiments described above. For example, the bending mechanism according to the first embodiment is applied to a treatment instrument such as a multidegree-of-freedom surgical instrument in the shown example, but may be applied to a manipulator. Moreover, the third embodiment can be combined with the modifications of the second embodiment. It should be understood that the invention can be embodied in various other ways without departing from the spirit thereof.

Now, other characteristic technical matters according to the present application are additionally set forth below.

Notes (Additional note 1) A rod section which is elastically deformable in directions other than an axial direction is provided.

(Additional note 2) The directions of the elastic deformation are one-dimensional.

(Additional note 3) The directions of the elastic deformation are two-dimensional.

(Additional note 4) The rod section is provided on the distal end side of a double joint mechanism.

(Additional note 5) A rod section which varies in the cross sectional area of a link (rod body) is provided.

(Additional note 6) A rod section which varies in Young's modulus is provided.

(Additional note 7) The rod section is divided by a separate member.

(Additional note 8) A rod section in which the cross sectional area of a link (rod body) is equal and in which the link (rod body) is twisted is provided.

(Additional note 9) A link having a truss structure is provided.

(Additional note 10) A link (rod body) having a structure that is not easily buckled is provided.

The present invention is advantageous to technical fields that use a bending joint mechanism used in a multidegree-of-freedom surgical instrument, a surgical instrument having this bending joint mechanism, and a manipulator having this bending joint mechanism. The present invention is also advantageous to technical fields that manufacture the above.

The present invention is not completely limited to the embodiments described above, and modifications of components can be made at the stage of carrying out the invention without departing from the spirit thereof. Further, various inventions can be made by properly combining the components disclosed in the embodiments described above.

What is claimed is:

1. A bending joint mechanism comprising a joint section, the joint section comprising:
    a shaft section which has an arc-shaped first rotation guide portion around a first rotation center and which has an axis that intersects at right angles with the axis of the first rotation center;
    an actuating section having an arc-shaped second rotation guide portion around a second rotation center, the second rotation guide portion coming in rolling contact with the first rotation guide portion at a proximal end portion thereof;
    a coupling member which is rotatably coupled at a distal end portion thereof to the second rotation center and which is rotatably coupled at a proximal end portion thereof to the first rotation center; and
    a rod section which is provided translatability relative to the shaft section in the axial direction of the shaft section and which is coupled at a distal end portion thereof to a position other than the first rotation center and which translates in the axial direction of the shaft section in response to a driving force,
    wherein the bending joint mechanism turns the second rotation guide portion around the first rotation center along the first rotation guide portion via the coupling member together with the translating of the rod section to bend the actuating section relative to the shaft section, and
    the rod section has an elastic portion which is elastically deformable in directions other than the axial direction of the shaft section.

2. The bending joint mechanism according to claim 1, wherein the directions of the elastic deformation of the rod section are one-dimensional in the directions other than the axial direction of the shaft section.

3. The bending joint mechanism according to claim 1, wherein the directions of the elastic deformation of the rod section are two-dimensional in the directions other than the axial direction of the shaft section.

4. The bending joint mechanism according to claim 1, wherein the cross sectional area of the rod section varies in the axial direction of the rod section.

5. The bending joint mechanism according to claim 1, wherein the Young's modulus of the rod section varies in the axial direction of the rod section.

6. The bending joint mechanism according to claim 1, wherein the rod section is dividable into a plurality of components different in material.

7. A surgical instrument having the bending joint mechanism according to claim 1.

8. A manipulator having the bending joint mechanism according to claim 1.

9. A bending joint mechanism comprising a first joint section, the first joint section comprising:
- a first shaft section which has an arc-shaped first rotation guide portion around a first rotation center and which has an axis that intersects at right angles with the axis of the first rotation center;
- a first actuating section having an arc-shaped second rotation guide portion around a second rotation center, the second rotation guide portion coming in rolling contact with the first rotation guide portion at a proximal end portion thereof;
- a first coupling member which is rotatably coupled at a distal end portion thereof to the second rotation center and which is rotatably coupled at a proximal end portion thereof to the first rotation center;
- a first rotation gear which has the same axis and radius of a rotation center as the axis and radius of the first rotation center of the first rotation guide portion;
- a second rotation gear which has the same axis and radius of the second rotation center as the axis and radius of a rotation center of the second rotation guide portion and which engages with the first rotation gear; and
- a first rod section which is coupled to the first coupling member and configured for translation, the bending joint mechanism further comprising a second joint section which is provided side by side with the first joint section along the axial direction of the first shaft section and which is disposed forward of the first joint section and which is coupled to the first actuating section, the second joint section comprising:
- a second shaft section which has an arc-shaped first rotation guide portion around a first rotation center and which has an axis that intersects at right angles with the axis of the first rotation center;
- a second actuating section having an arc-shaped second rotation guide portion around a second rotation center, the second rotation guide portion coming in rolling contact with the first rotation guide portion;
- a second coupling member which is rotatably coupled at a distal end portion thereof to the second rotation center and which is rotatably coupled at a proximal end portion thereof to the first rotation center; and
- a second rod section which is coupled at a distal end portion thereof to a position other than the first rotation center of the second coupling member and which is rotatably coupled at a proximal end portion thereof to the second rotation gear at a position parallel to the axis of the rotation center of the second rotation gear and other than the rotation center and which translates in the axial direction of the second shaft section in response to a driving force, wherein the central axis of the second rotation center of the first actuating section and the central axis of the first rotation center of the second joint section are arranged at skew positions, that is, are arranged to be parallel but not flush, the first rotation gear is rotated by an independent second driving force different from a first driving force that translates the first rod section, whereby the second rotation gear rotates, the second rod section serves as driving force transmitting means to rotate the second coupling member around the first rotation center in response to the rotation of the second rotation gear, the second rotation guide portion of the second joint section turns around the first rotation center of the second joint section along the first rotation guide portion of the second joint section in response to the rotation of the second coupling member, and the second actuating section is bent relative to the second shaft section by the turning of the second rotation guide portion of the second joint section, and the second rod section has an elastic part which is elastically deformable in a longitudinal sectional direction.

10. The bending joint mechanism according to claim 9, wherein the directions of the elastic deformation of the second rod section are two-dimensional in directions other than the axial direction of the second shaft section.

11. The bending joint mechanism according to claim 9, wherein the cross sectional area of the second rod section varies in the axial direction of the second rod section.

12. The bending joint mechanism according to claim 9, wherein the Young's modulus of the second rod section varies in the axial direction of the second rod section.

13. The bending joint mechanism according to claim 9, wherein the second rod section is dividable into a plurality of components different in material.

14. A surgical instrument having the bending joint mechanism according to claim 9.

15. A manipulator having the bending joint mechanism according to claim 9.

* * * * *